United States Patent
Ates et al.

(10) Patent No.: US 8,981,121 B2
(45) Date of Patent: Mar. 17, 2015

(54) PROCESS FOR THE PREPARATION OF NITROGEN SUBSTITUTED AMINOTETRALINS DERIVATIVES

(75) Inventors: Celal Ates, Brussels (BE); Arnaud Schule, Brussels (BE); Magali Palacio, Brussels (BE); Paul Deutsch, Brussels (BE); David Vasselin, Brussels (BE); Nicolas Carly, Brussels (BE); Ganesh Phadtare, Maharashtra (IN); Swapnil Yerande, Maharashtra (IN); Jean-Pierre Delatinne, Brussels (BE); Maria Luisa Escudero Hernandez, Parma (IT); Veronique Pinilla, Brussels (BE)

(73) Assignee: UCB Pharma GmbH, Monheim (DE)

( * ) Notice: Subject to any disclaimer, the term of this patent is extended or adjusted under 35 U.S.C. 154(b) by 8 days.

(21) Appl. No.: 13/806,378

(22) PCT Filed: Jun. 24, 2011

(86) PCT No.: PCT/EP2011/060655
§ 371 (c)(1),
(2), (4) Date: Dec. 21, 2012

(87) PCT Pub. No.: WO2011/161255
PCT Pub. Date: Dec. 29, 2011

(65) Prior Publication Data
US 2013/0102794 A1   Apr. 25, 2013

(30) Foreign Application Priority Data

Jun. 25, 2010   (EP) .................................... 10006621

(51) Int. Cl.
*C07D 333/20*  (2006.01)
*C07B 57/00*  (2006.01)
*C07C 213/10*  (2006.01)
*C07C 217/52*  (2006.01)
*C07C 271/24*  (2006.01)
*C07C 213/08*  (2006.01)
*C07C 51/353*  (2006.01)
*C07C 213/00*  (2006.01)
*C07C 271/02*  (2006.01)
*C07C 269/08*  (2006.01)
*C07C 217/54*  (2006.01)
*C07C 51/41*  (2006.01)

(52) U.S. Cl.
CPC .............. *C07C 213/10* (2013.01); *C07B 57/00* (2013.01); *C07C 217/52* (2013.01); *C07C 2102/10* (2013.01); *C07C 271/24* (2013.01); *C07C 213/08* (2013.01); *C07C 51/353* (2013.01); *C07D 333/20* (2013.01); *C07C 213/00* (2013.01); *C07B 2200/07* (2013.01); *C07C 271/02* (2013.01); *C07C 269/08* (2013.01); *C07C 217/54* (2013.01); *C07C 51/412* (2013.01)
USPC ........................................................... 549/74

(58) Field of Classification Search
CPC ........................................................ C07B 57/00
USPC ................................................... 549/45, 74
See application file for complete search history.

(56) References Cited

U.S. PATENT DOCUMENTS

| 4,968,837 A | 11/1990 | Manimaran et al. |
| 2007/0185346 A1 | 8/2007 | Vaidya |

FOREIGN PATENT DOCUMENTS

| EP | 1975161 A1 | 10/2008 |
| JP | 09-40667 A | 2/1997 |
| JP | 2001-294582 A | 10/2001 |
| JP | 2004-123596 A | 4/2004 |
| WO | 01/17944 A1 | 3/2001 |

(Continued)

OTHER PUBLICATIONS

Cusack, N.J. et al., "N-0923. Dopamine D2 agonist.", Drugs of the Future, Prous Science, Es, 18(11), 1993, 1005-1008.

(Continued)

*Primary Examiner* — Taofiq A Solola
(74) *Attorney, Agent, or Firm* — McDonnell Boehnen Hulbert & Berghoff LLP

(57) ABSTRACT

The present invention provides an alternative synthesis of N-substituted aminotetralines comprising resolution of N-substituted aminotetralins of formula (II), wherein $R^1$, $R^2$ and $R^3$ are as defined for compound of formula (I).

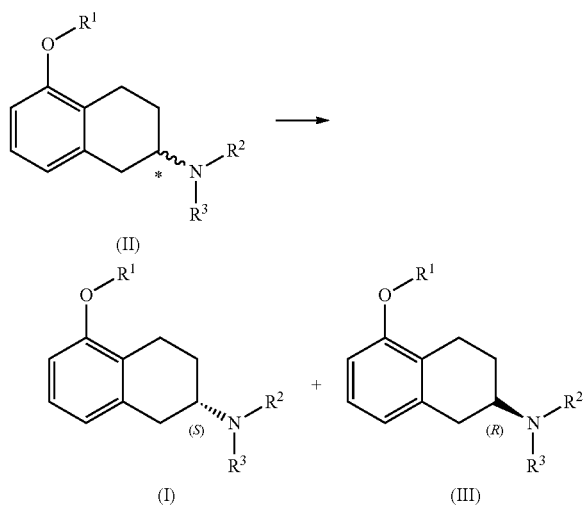

16 Claims, No Drawings

(56) References Cited

FOREIGN PATENT DOCUMENTS

WO          01/83807 A1      11/2001
WO       2010/043571 A1      4/2010

OTHER PUBLICATIONS

Sonesson, C. et al., "Synthesis and Evaluation of Pharmacological and Pharmacokinetic Properties of Monopropyl Analogs of 5-, 7,- and 8- not Trifluoromethyl) Sulfonyl 3/4 Sulfonyl 3/4 Oxy 3/4 -2-Aminotetralins: Central Dopamine and Serotonin Receptor Activity.", European Journal of Medicinal Chemistry, vol. 38, 1995, 1319-1329.
Brown, D. A. et al., "Investigation of Various N-heterocyclic Substituted Piperazine Versions of 5/7-{[2- (4-aryl-piperazin-1-yl)-ethyl]-propyl-amino}-5,6,7,8-tetrahydro-naphthalen-2-ol: Effect on affinity and selectivity for dopamine D3 receptor", Bioorganic & Medicinal Chemistry, 17(11), 2009, 3923-3933.
Ghosh, B. et al., "Development of (s)-N6(2-(4-(Isoquinolin-1-yl)piperazin-1-yl)ethyl)-N 6-propyl-4,5,6,7-tetrahydrobenzo[d]-thiazole-2,6-diamine and Its Analogue as a D3 Receptor Preferring Agonist: Potent in Vivo Activity in Parkinsons Disease Animal Models", Journal of Medicinal Chemistry, vol. 53, 2010, 1023-1037.
Hoeve, T. W. et al., "The design of resolving agents. Chiral cyclic phophoric acids", Journal of Organic Chemistry, vol. 50, 1985, 4508-4514.
Wikstroem, H. et al., "Resolved monophenolic 2-aminotetralins and 1,2,3,4,4a,5,6, 10b-octahydrobenzo[f]quinolines structural and stereochemical considerations for centrally acting pre- and postsynaptic dopamine-receptor agonists", Journal of Medicinal Chemistry, 28(2), 1985, 215-225.
Anonymous, "Chiral resolving agents", Internet Citation, 2010, 1-15.
Selditz, U. et al., "Termperature Effects on the Chromatographic Behaviour of Racemic 2-Amidotetralins on a Whelk-0 1 Stationary Phase in Super-and Subcritical Fluid Chromatography", Die Pharmazie, 54(3), 1999, 183-191.
Chumpradit, S. et al., "Synthesis, Resolution and Radioiodination of S(-) Trans-5-Hydroxy-2- not N-N-Propyl-N(3'-Iodo-2-Propenyl)Amino 3/4 Tetralin-S(-)Trans-5-OH-Pipat: A New Dopamine D2-Like Receptor Ligand", Journal of Labelled Compounds and Radiopharmaceuticals, 36(11), 1995, 1051-1062.
Jansen, J. M. et al., "Semipreparative Enantiomeric Separation of a Series of Putative Melatonin Receptor Agents Using Tri-acetylcellulose as Chiral Stationary Phase", Chirality, vol. 6, 1994, 596-604.
Gerding, T. K. et al., "Separation of N-0437 Enantiomers by RP-HPLC After Pre-Column Derivatization with D-Dextro Clucuronic Acid", Journal of High Resolution Chromatography and Chromatography Communications, 10(9), 1987, 523-525.
Brown, D. A. et al., "Investigation of Various N-heterocyclic Substituted Piperazine Versions of 5/7-{[2- (4-aryl-piperazin-1-yl)-ethyl]-propyl-amino}-5,6,7,8-tetrahydro-naphthalen-2-ol: Effect on affinity and selectivity for dopamine D3 receptor.", Bioorganic & Medicinal Chemistry, 17(11), 2009, 3923-3933.
Balaram, G. et al., "Development of (s)-N6-(2-(4-(Isoquinolin-1-yl)piperazin-1-yl)ethyl)-N 6-propyl-4,5,6,7-tetrahydrobenzo[d]-thiazole-2,6-diamine and Its Analogue as a D3 Receptor Preferring Agonist: Potent in Vivo Activity in Parkinsons Disease Animal Models", Journal of Medicinal Chemistry, vol. 53, 2010, 1023-1037.
Wikstroem, H. et al., "Resolved monophenolic 2-aminotetralins and 1,2,3,4,4a,5,6, 10b-octahydrobenzo[f] quinolines structural and stereochemical considerations for centrally acting pre- and postsynaptic dopamine-receptor agonists", Journal of Medicinal Chemistry, 28(2), 1985, 215-225.
Selditz, U. et al., "Temperature Effects on the Chromatographic Behaviour of Racemic 2-Amidotetralins on a Whelk-0 1 Stationary Phase in Super-and Subcritical Fluid Chromatography", Die Pharmazie, 54(3), 1999, 183-191.
Chumpradit, S. et al., "Synthesis, Resolution and Radioiodination of S(-) Trans-5-Hydroxy-2- not N-N-Propyl-N(3'-Iodo-2-Propenyl)Amino 3/4 Tetralin-S(-)Trans-5-OH-Pipat: A New Dopamine D2-Like Receptor Ligand", Journal of Labelled Compounds and Radiopharmaceuticals, 36(11), 1995, 1051-1062.
Gerading, T. K. et al., "Separation of N-0437 Enantiomers by RP-HPLC After Pre-Column Derivatization with D-Dextro Clucuronic Acid", Journal of High Resolution Chromatography and Chromatography Communications, 10(9), 1987, 523-525.

PROCESS FOR THE PREPARATION OF NITROGEN SUBSTITUTED AMINOTETRALINS DERIVATIVES

This application is a US national phase of International Application No. PCT/EP2011/060655 filed on Jun. 24, 2011, which claims priority to European Patent Application No. 10006621.6 filed on Jun. 25, 2010, the disclosures of which are incorporated herein by reference in their entirety.

The present patent application relates to a novel process for the preparation of nitrogen-substituted aminotetralins.

Particularly, the present patent application relates to a novel process for the preparation of substantially optically pure nitrogen-substituted aminotetralins.

In a particular embodiment, the present application relates to an improved process for the manufacture of rotigotine.

Rotigotine is the International Non-Proprietary Name (INN) of compound (−)-5,6,7,8-tetrahydro-6-[propyl-[2-(2-thienyl)ethyl]amino]-1-naphthalenol having the structure shown below.

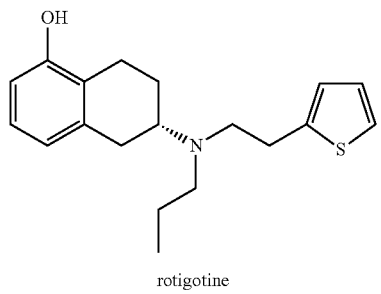 [SMILES: CCCN(CCc1cccs1)[C@H]1CCc2c(O)cccc2C1]

rotigotine

Rotigotine is a non-ergolinic D1/D2/D3 dopamine agonist that resembles dopamine structurally and has a similar receptor profile but a higher receptor affinity.

In contrast to other non-ergolinic dopamine agonists, rotigotine has significant D1 activity, which may contribute to a more physiological action.

In contrast to ergolinic compounds, rotigotine has a very low affinity for 5 HT2B receptors and thus a low risk of inducing fibrosis.

Actions on non-dopaminergic receptors (such as 5-HT1A agonism and A2B antagonism) may contribute to other beneficial effects, such as antidyskinetic activity, neuroprotective activity and antidepressive effects.

Rotigotine is disclosed as active agent for treating patients suffering from Parkinson's disease (described in WO 2002/089777), Parkinson's plus syndrome (described in WO 2005/092331), depression (described in WO 2005/009424) and the restless-legs syndrome (described in WO 2003/092677) as well as for the treatment or prevention of dopaminergic neurone loss (described in WO 2005/063237) and treatment of pain (PCT/EP2007/005381).

International patent application WO01/38321 describes a process of manufacture of nitrogen substituted aminotetralins and in particular rotigotine.

International patent application WO2010/043571 describes a process for the manufacture of rotigotine involving diastereoisomeric salt resolution of aminotetralins.

U.S. Pat. No. 4,968,837 describes the diastereoisomeric resolution of 1,2,3,4-tetrahydro-5-methoxy-N-propyl-naphthalen-2-amine with L-dibenzoyl-tartaric acid.

US patent application no 2007/185346 relates to a method and a tray or kit useful for selecting resolution agents, combinations and conditions to separate optical isomers.

Cusack N. J. et al. in Drugs of the Future (Prous Science, ES, Vol. 18, no 11, 1 Jan. 1993, pages 1005-10008) describes a process of manufacture of rotigotine involving diasteroisomeric resolution of 2-(N-propylamino)-5-methoxytetraline.

European patent application EP 1 975 161 A1 relates to the use of heterocyclyl-substituted-tetrahydro-naphtalen-amine compounds for the treatment of diseases mediated by 5-HT7 receptor affinity.

Wikstoem H. et al. in Journal of Medicinal Chemistry (American Chemical Society, Washington, US, vol. 28, no 2, 1 Jan. 1985, pages 215-225) describes diastereoisomeric resolution of 2-(N-propylamino)-5-methoxytetraline with (R)-(−)-β-methylmandelic acid.

Brown et al. in Bioorganic and Medicinal Chemistry (Pergamon, GB, vol. 17, no 11, 1 Jun. 2009, pages 3923-3933), Balaram Ghosh et al. in Journal of Medicinal Chemistry (American Chemical Society, Washington, US, vol. 53, 1 Jan. 2010, pages 1023-1037), Hove Ten W. et al. In Journal of Organic Chemistry (American Chemical Society, Easton; US, vol. 50, 1 Jan. 1985, pages 4508-4514), Sonesson C. et al. in European Journal of Medicinal Chemistry (Editions Scientifiques Elsevier, Paris, FR, vol. 38, 1 Jan. 1995, pages 1319-1329) and Chinese patent application no CN 1017717392A relate to the use of chiral phosphonic acids and in particular Chlocyphos as agents for diastereoisomeric resolution.

International patent application WO2010/043571 describes a process for the preparation of (S)-(−)-2-(N-propylamino)-5-methoxytetraline and (S)-(−)-2-(N-propylamino)-5-hydroxytetraline by optical resolution of the corresponding racemic mixtures with an optically active organic acids such as (+)-N-(3,5-dinitrobenzoyl)-α-phenylglycine.

Selditz U. et al. in Die Pharmazie (Govi Verlag Pharmazeutischer Verlag Gmbh, Eschborn, DE, vol. 54, no 3, 1 Jan. 1999, pages 183-191) describes chiral separation of 2-amido tetralins using supercritical $CO_2$.

Chumpradit S. et al. in Journal of Labelled Compounds and Radiopharmaceuticals (John Wiley, Chichester, GB, vol. 36, no 11, 1 Jan. 1995, pages 1051-1062 discloses chiral separation of 2-acetamidotetralins.

Jansen J. M. et al. in Chirality (Wiley-Liss, New York, US, vol. 6, 1 Jan. 1994, pages 596-604, describes chiral separation of 2-amido tetralins using a cellulose based stationary phase.

The present invention provides for an alternative and better process for the manufacture of rotigotine.

In particular, the present invention relates to a process of manufacture of synthetic intermediates which are useful for the preparation of nitrogen substituted aminotetralins and in particular useful for the synthesis of rotigotine, and salts thereof.

In a first aspect, the present invention relates to a process of manufacture of optically enriched (S)—N-substituted aminotetralins of formula (I), wherein $R^1$ is alkyl; and $R^2$ and $R^3$ are independently hydrogen, alkyl, alkoxycarbonyl, aryloxycarbonyl, arylcarbonyl or alkylcarbonyl.

comprising resolution of N-substituted aminotetralins of formula (II), wherein $R^1$, $R^2$ and $R^3$ are as defined for compound of formula (I), as shown in scheme 1.

Scheme 1

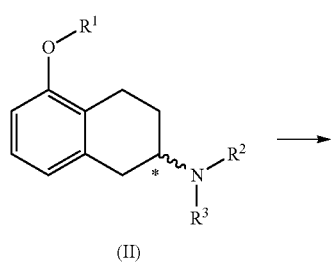

(II)

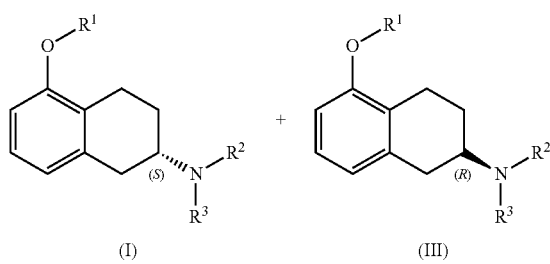

(I)                (III)

The term "optically enriched" as used herein when referring to a particular compound means that more than 50%, preferably more than 75%, more preferably more than 85%, most preferably more than 94% of the compound has the stereogenic center indicated by (*) in a given configuration (R) or (S).

In a second aspect, the present invention relates to a process of manufacture of substantially optically pure (S)—N-substituted aminotetralins of formula (I), wherein
R$^1$ is alkyl; and
R$^2$ and R$^3$ are independently hydrogen, alkyl, alkoxycarbonyl, aryloxycarbonyl, arylcarbonyl or alkylcarbonyl.
comprising resolution of N-substituted aminotetralins of formula (II).

Compounds of formula (I), (II) and (III) according to the present invention may be present in free base or in salt form.

Said salt generally results from the reaction of the free base of said compounds with a mineral acid of formula HX.

The term "substantially optically pure" as used herein when referring to a particular compound means that at least 95%, preferably at least 96%, more preferably at least 97%, most preferably at least 98%, even most preferably at least 99% of the compound has the stereogenic center indicated by (*) in a given configuration (R) or (S).

The term "alkyl", as used herein, is a group which represents saturated, monovalent hydrocarbon radicals having straight (unbranched) or branched moieties, or combinations thereof, and containing, 1-20 carbon atoms, preferably 1-8 carbon atoms, more preferably 1-6 carbon atoms; most preferably alkyl groups have 1-4 carbon atoms.

"Alkyl" groups according to the present invention may be unsubstituted or substituted. Preferred alkyl groups are C$_{1-4}$ alkyl. Examples of such C$_{1-4}$ alkyl are methyl, ethyl, n-propyl, isobutyl, tert-butyl.

The term "alkoxycarbonyl" as used herein refers to the group —C(O)OR$^a$ wherein R$^a$ is an alkyl group as defined above.

The term "aryloxycarbonyl" as used herein refers to the group —C(O)OR$^b$ wherein R$^b$ is an aryl group as defined herein.

The term "aryl" as used herein refers to an unsaturated aromatic carbocyclic group of from 6 to 14 carbon atoms having a single ring (e.g. phenyl) or multiple condensed rings (e.g. naphthyl).

The term "arylcarbonyl" as used herein refers to a group —C(O)R$^b$ wherein R$^b$ is an aryl group as defined above.

The term "alkylcarbonyl" as used herein refers to a group —C(O)R$^a$ wherein R$^a$ is an alkyl group as defined above.

The term "resolution" as used herein refers to the separation of a mixture of enantiomers into its corresponding individual enantiomers.

The enantiomers may be present in said mixture in various ratios of enantiomer versus the other.

Particularly, the mixture is a racemic mixture. A racemic mixture as herein defined is a mixture comprising 50% of one enantiomer and 50% of the other enantiomer.

Resolution can be achieved by various methods including conversion to diastereoisomers, differential absorption, chiral recognition, biochemical processes, mechanical separation, kinetic resolution and deracemization as detailed in Jerry March in "Advanced Organic Chemistry", fourth edition, Chapter 4, pages 120-125.

In one embodiment, the present invention relates to a process of manufacture of substantially optically pure compound of formula (I) by diastereoisomeric salt resolution of compound of formula (II) as shown in following scheme 2.

Scheme 2

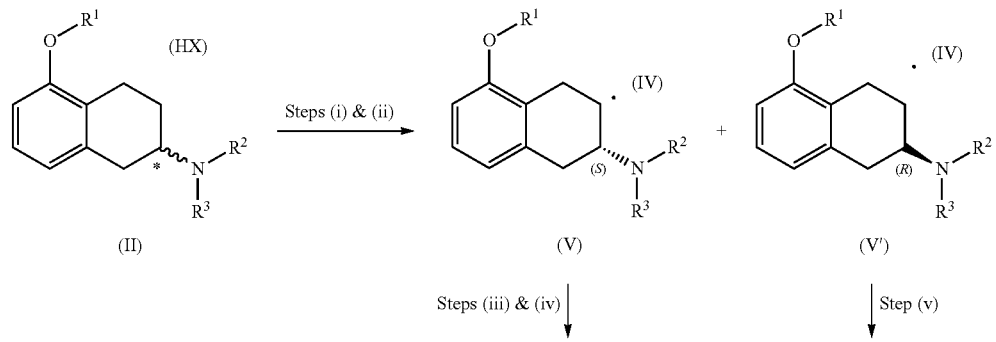

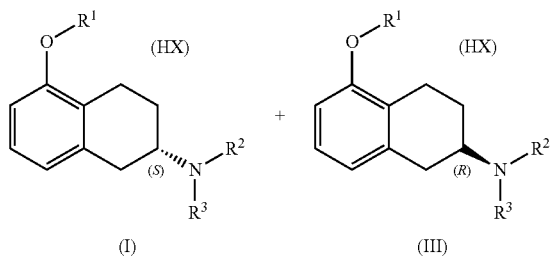

In a particular embodiment according to the present invention, diastereoisomeric salt resolution of compound of formula (II) is performed by:
  (i) reacting free base of compound of formula (II) with a substantially optically pure acid (IV) in a solvent to afford diasteroisomeric salts (V) and (V');
  (ii) crystallizing resulting diastereroisomeric salt (V) in a solvent;
  (iii) reacting said diastereoisomeric salt (V) with a base to afford compound of formula (I); and
  (iv) optionally reacting compound of formula (I) obtained in step (iii) with a mineral acid in a solvent to afford a salt of compound of formula (I).

In another particular embodiment according to the present invention, diastereoisomeric salt resolution of compound of formula (II) is typically performed by:
  (i) reacting free base of compound of formula (II) with a substantially optically pure acid (IV) in a solvent to afford diasteroisomeric salts (V) and (V');
  (ii) filtering diastereroisomeric salt (V') out of the reaction media;
  (iii) reacting diastereoisomeric salt (V) present in the mother liquors with a base to afford compound of formula (I); and
  (iv) optionally reacting compound of formula (I) obtained in step (iii) with a mineral acid in a solvent to afford a salt of compound of formula (I).

Alternatively, steps (iii) and (iv) in the above embodiments can be replaced by reacting diastereoisomeric salt (V) with a mineral acid to afford directly salt of compound of formula (I).

If compound of formula (II) is in salt form, for example hydrochloride or hydrobromide salt, then such salt shall be treated with a base prior to steps (i) of the above mentioned processes.

Substantially optically pure compounds of formula (I), (V) and (V') may be optionally recrystallized or reslurried in a solvent in order to increase the optical purity of said compounds as will be deemed necessary by the person skilled in the art.

In a further particular embodiment according to the present invention and as shown in scheme 3, the undesired diastereoisomeric salt (V') may be recycled into the HX salt of compound of formula (II) which can then undergo again the processes described in scheme 2 to afford compound of formula (I).

Scheme 3

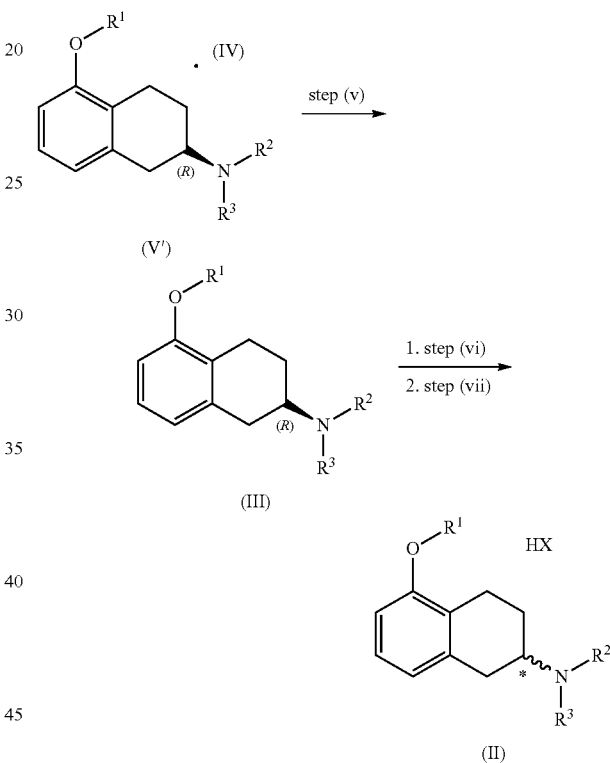

Such transformation typically occurs by:
  (v) treating diastereoisomeric salt (V') with a base to afford the undesired enantiomer (III);
  (vi) racemizing enantiomer (III) into the free base of compound of formula (II) by treatment with a racemization agent;
  (vii) treating compound of formula (II) with HX to afford HX salt of compound (II).

These additional steps provide the particular advantage of recycling the undesired salt (V') into the initial racemic compound of formula (II) which ultimately can be transformed into the desired enantiomer (I) through an iterative process, thereby increasing overall yield of the process and reducing formation of waste material.

In a particular embodiment according to the present invention, compound of formula (II) is a racemic mixture as defined herein.

Compounds of formula (II) which are particularly suitable to undergo diastereoisomeric salt resolution according to the present invention are compounds of formula (II) wherein $R^1$ and $R^2$ are alkyl and $R^3$ is hydrogen.

Said compounds of formula (II) may be in form of a free base or in salt form. Examples of salts of compounds of formula (II) are hydrochloride and hydrobromide salts.

Compounds of formula (II) wherein $R^1$ and $R^2$ are alkyl and $R^3$ is hydrogen may be obtained through reductive alkylation of corresponding tetralone (VI) by reaction with an amine of formula (VII), wherein $R^2$ and $R^3$ are as defined for compound of formula (II), in a solvent and in the presence of hydrogen or a hydride, as shown in scheme 4, or according to any other method known to the person skilled in the art.

Scheme 4

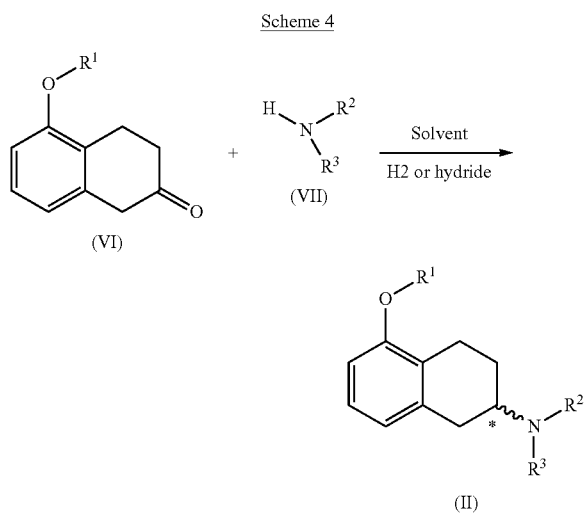

Compounds of formula (II) obtained according to scheme 4 may be isolated as such or generated in situ in the reaction media and transformed directly into diastereoisomeric salts (V) by reaction with a substantially optically pure acid (IV) in a solvent.

Alternatively compounds of formula (II), wherein $R^3$ is hydrogen, may be obtained by reacting a mineral salt of tetraline of formula (X) with an aldehyde of formula (XI), as shown in the following scheme 5, according to methods known to the person skilled in the art.

Scheme 5

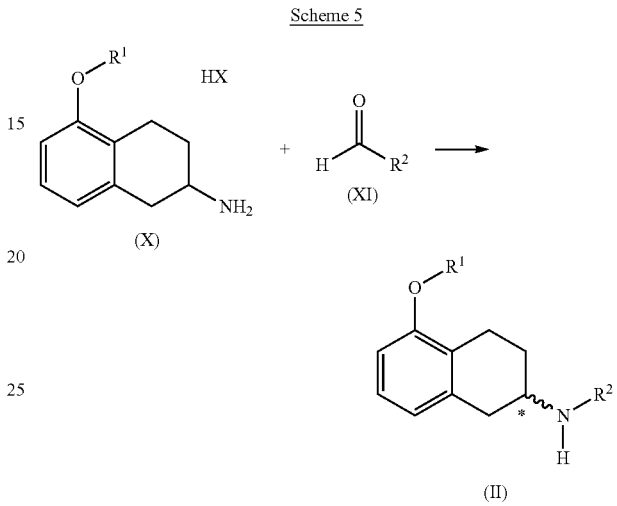

In a further particular embodiment, the present invention relates to a process of manufacture of substantially optically pure (S)-1,2,3,4-tetrahydro-5-methoxy-N-propyl-naphthalen-2-ammonium hydrochloride (Ia) by diastereoisomeric salt resolution of a racemic mixture of (1,2,3,4-tetrahydro-5-methoxy-N-propyl-naphthalen-2-ammonium hydrochloride (IIa) in the presence of a substantially optically pure acid (IV) and in a solvent, as shown in the following scheme 6.

Scheme 6

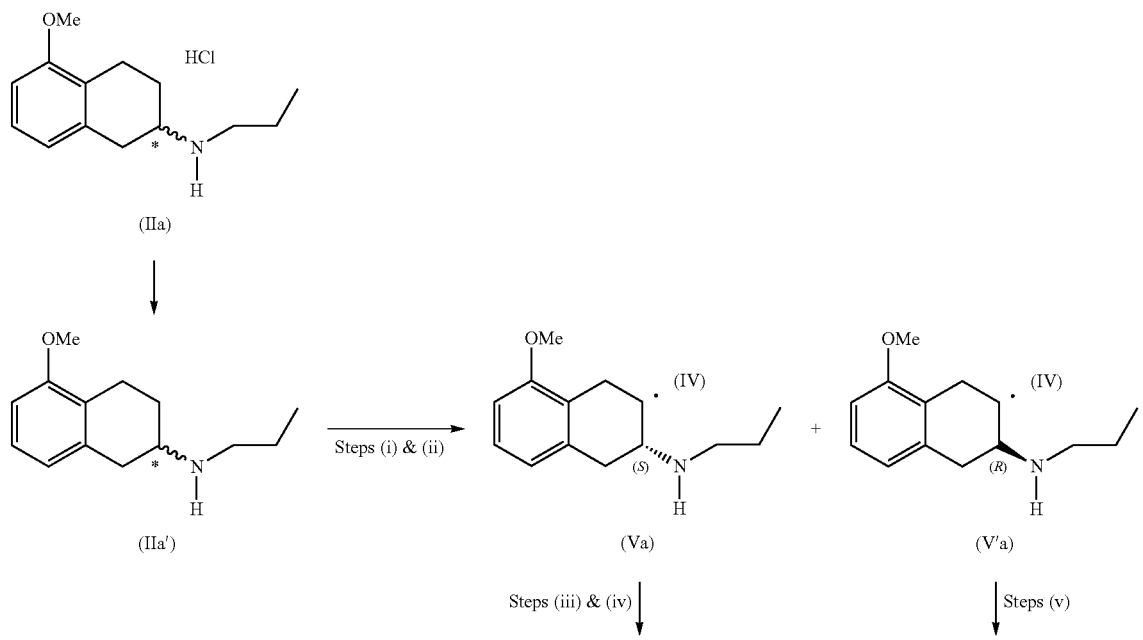

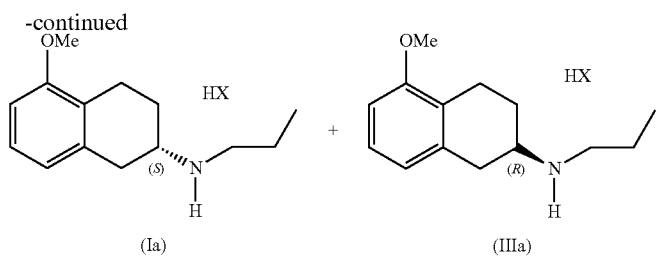

(Ia)          (IIIa)

A compound of formula (IIa) is initially transformed into the corresponding free base (IIa') by reaction with a base according to methods known by the person skilled in the art.

Compounds of formula (IIa) according to the present invention may be obtained by reacting 5-methoxy-2-tetralone (VIa) with n-propyl amine (VIIa) as described in Journal of Medicinal Chemistry Chemistry 1991 34, 3235-3241 or according to any other method known by the person skilled in the art.

Alternatively, compounds of formula (IIa) according to the present invention may be obtained by reacting 5-methoxy-tetraline hydrochloride (Xa) with propionaldehyde (XIa) according to methods known to the person skilled in the art.

Compound of formula (IIa') is then reacted with a substantially optically pure acid of formula (IV) as outlined in step (i) of Scheme 6.

Examples of solvents that may be used in step (i) of the process according to the present invention are water, alcohols such as methanol, ethanol, propan-1-ol, propan-2-ol; ethers such as MTBE (methyl tert-butyl ether), THF (tetrahydrofuran), Me-THF (2-methyl THF); esters, such as methyl acetate, ethyl acetate, isopropyl acetate; a mixture of two or more of these solvents.

In a particular embodiment according to the invention, the solvent is a mixture of water and an organic solvent selected from methanol, ethanol, propan-1-ol, propan-2-ol, methyl tert-butyl ether (MTBE), THF (tetrahydrofuran), Me-THF (2-methyl THF), methyl acetate, ethyl acetate or isopropyl acetate; a mixture of two or more of these solvents.

Examples of base that may be used in step (i) of the process according to the present invention are inorganic bases such as sodium hydroxide, potassium hydroxide, sodium carbonate, potassium carbonate, potassium hydrogen phosphate, sodium hydrogen phosphate, potassium phosphate, sodium phosphate, or organic bases such as for example diisopropylamine, triethylamine, piperidine, pyrrolidine.

Preferred base is selected from the group consisting of sodium carbonate, potassium carbonate, diisopropyl amine and triethylamine.

The proportion of substantially optically pure acid with respect to compound of formula (IIa') is generally of at least 0.5 molar equivalents.

Examples of substantially optically pure acids (IV) according to the present invention are (R)-2-methoxy-2-phenyl acetic acid (IVa), (R)-2-(2-chlorophenyl)-2-hydroxyacetic acid (IVb), (S)-2-hydroxy-3-phenylpropionic acid (IVc), (S)-(+)-2-(6-methoxy-2-naphthyl)-propionic acid (IVd) or (R)-(−)-2-(6-methoxy-2-naphthyl)-propionic acid (IVd), and (R)-2-(5-chloro-2-oxo-2,3-dihydroindol-1-yl)-propionic acid (IVh).

Preferred substantially optically pure acids of formula (IV) according to the present invention are (R)-2-methoxy-2-phenyl acetic acid (IVa), (R)-2-(2-chlorophenyl)-2-hydroxyacetic acid (IVb) and (S)-2-hydroxy-3-phenylpropionic acid (IVc). It is noteworthy that these acids give very good results even though their use as resolution agents has been scarcely described in literature.

Reaction of the free base (IIa') with a substantially optically pure acid (IV) affords mixture of diastereoisomeric salts (Va) and (V'a).

The desired diastereoisomeric salt (Va) may be crystallized or slurried directly in the reaction media and then filtered out of the reaction media.

Solvent used for crystallization described in step (ii) are generally the same as the one used in step (i). When a mixture of water and an organic solvent is used in step (i), the aqueous phase is discarded prior to crystallization and the remaining organic phase is cooled to allow crystallization to proceed. Isolation temperature is preferably comprised between −10° C. and 0° C.

Optionally, the organic phase may be dried by drying techniques known by the man skilled in the art.

In a particular embodiment, the organic phase is seeded with optically pure compound of formula (Ia) to trigger crystallization.

The desired isolated diastereoisomeric salt (Va) is then further reacted with a base to afford the free base of compound of formula (Ia), according to methods known to the person skilled in the art, as shown in step (iii) of scheme 6. Compound of formula (Ia) is then reacted with a mineral acid HX to afford corresponding salts of compound of formula (Ia) (step (iv) of Scheme 6.

Solvents which are used in step (iii) are alcohols such as methanol, ethanol, propan-1-ol, propan-2-ol; ethers such as MTBE (methyl tert-butyl ether), THF (tetrahydrofuran), Me-THF (2-methyl THF); esters, such methyl acetate, ethyl acetate, isopropyl acetate; or a mixture of two or more of these solvents.

Base which may be used in step (iii) is selected from sodium hydroxide, potassium hydroxide, sodium carbonate, potassium carbonate, potassium phosphate, sodium phosphate and triethylamine.

Compound of formula (Ia) may be isolated in the form of a free base or in the form of a mineral salt, such as hydrochloride or hydrobromide.

In a particular embodiment according to the present invention, salts of compounds of formula (Ia) are obtained by reacting directly the diastereoisomeric salts (Va) isolated under step (ii) with a mineral acid HX in a solvent, without isolating the free base form of compound of formula (Ia).

Examples of such mineral acid are hydrochloric acid (HCl), hydrobromic acid (HBr), hydroiodic acid (HI), sulfuric acid ($H_2SO_4$) and phosphoric acid ($H_3PO_4$). Preferred mineral acids are hydrochloric acid and hydrobromic acid.

Examples of solvents that may be used in step (iv) of the process according to the present invention are water, ethers such as diethyl ether, MTBE (methyl tert-butyl ether), THF (tetrahydrofuran), Me-THF (2-methyl THF); aromatic hydrocarbons such as toluene, xylene, alcohols, such as for example methanol, ethanol, propanol, butanol; ketones, such as acetone, methyl ethyl ketone, methyl isobutyl ketone; mixtures of two or more of these solvents.

Preferred solvent are water, ethers such as diethyl ether, MTBE (methyl tert-butyl ether), THF (tetrahydrofuran), Me-THF (2-methyl THF); and alcohols, such as for example methanol, ethanol, propanol, butanol or mixtures of two or more of these solvents.

In a particular embodiment, the present invention also relates to diastereoisomeric salts (Va) resulting from a combination of 1,2,3,4-tetrahydro-5-methoxy-N-propyl-naphthalen-2-amine (Ia) and any of the above mentioned acids (IV).

Examples of such salts (V) are (S)-1,2,3,4-tetrahydro-5-methoxy-N-propyl-naphthalen-2-ammonium (R)-2-methoxy-2-phenylacetate (Vaa), (S)-1,2,3,4-tetrahydro-5-methoxy-N-propyl-naphthalen-2-ammonium (R)-2-(2-chlorophenyl)-2-hydroxyacetate (Vab), (S)-1,2,3,4-tetrahydro-5-methoxy-N-propyl-naphthalen-2-ammonium (S)-2-hydroxy-3-phenylpropionate (Vac), (S)-1,2,3,4-tetrahydro-5-methoxy-N-propyl-naphthalen-2-ammonium (R) 2-(6-methoxy-2-naphthyl)-propionate (Vad), and (S)-1,2,3,4-tetrahydro-5-methoxy-N-propyl-naphthalen-2-ammonium (S)-2-(5-chloro-2-oxo-2,3-dihydroindol-1-yl)-propionate (Vah).

Preferred salts of formula (Va) according to the present invention are (S)-1,2,3,4-tetrahydro-5-methoxy-N-propyl-naphthalen-2-ammonium (R)-2-methoxy-2-phenylacetate (Vaa), (S)-1,2,3,4-tetrahydro-5-methoxy-N-propyl-naphthalen-2-ammonium (R)-2-(2-chlorophenyl)-2-hydroxyacetate (Vab) and (S)-1,2,3,4-tetrahydro-5-methoxy-N-propyl-naphthalen-2-ammonium (S)-2-hydroxy-3-phenylpropionate (Vac).

In another embodiment according to the present invention, diastereoisomeric salt (V'a) may be crystallized and filtered out of the reaction media. The diastereoisomeric salt (Va) present in the mother liquors may hence be reacted with a base or a mineral acid as mentioned here above to afford respectively the corresponding free base or the corresponding salt of compound of formula (Ia), which can be isolated from the reaction media according to methods know by the man skilled in the art.

In a particular embodiment according to the present invention, the chiral acid (IV) is added to a solution of compound (IIa') in a solvent as used in step (i) mentioned here above. The resulting mixture is heated, then cooled and filtered.

The solvent is removed and a solution of mineral acid, preferably hydrochloric acid is added. The solution is heated, then cooled and mineral salt of compound of formula (Ia) is isolated by filtration.

In said particular embodiment, (S)-2-methoxy-2-phenylacetic acid (IVa') is preferably used as chiral acid (IV) and (S)-1,2,3,4-tetrahydro-5-methoxy-N-propyl-naphthalen-2-ammonium-(S)-2-methoxy-2-phenylacetate (Vaa') is the diastereoisomeric salt thereby obtained.

In another particular embodiment according to the present invention, the undesired diastereoisomeric salt (V'a) may be recycled into compound of formula (IIa), as shown in scheme 7, which compound of formula (IIa) can then be reacted according to the conditions described in scheme 6 to afford compound of formula (Ia).

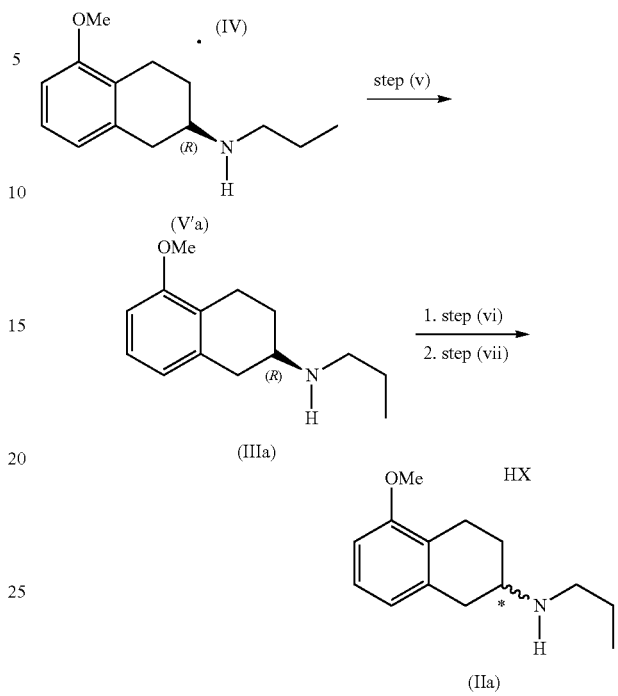

Scheme 7

Step (v) is typically achieved by treating diastereoisomeric salt (V'a), present in the mother liquors after diastereoisomeric salt (Va) has been filtered out, with a base, for example triethylamine, to afford the undesired enantiomer (IIIa).

Alternatively, step (v) may be performed on isolated diastereoisomeric salt (V'a) if said diastereoisomer has been filtered out of the reaction media, as mentioned here above.

Enantiomer (IIIa) may be racemized into compound of formula (IIa) by methods known to the person skilled in the art.

In a particular embodiment according to the present invention, enantiomer (IIIa) is transformed into compound of formula (IIa) by radical mediated racemization.

For example, enantiomer (IIIa) is reacted with an alkylthiol, such as dodecanethiol or octanethiol, in the presence of azobisisobutyronitrile, in a solvent (step (vi)). Resulting free base compound of formula (IIa') is subsequently treated with a mineral acid of formula HX, such as hydrochloric acid or hydrobromic acid, to afford compound of formula (IIa).

These additional steps provide the particular advantage of recycling the undesired salt (V'a) into the initial racemic compound of formula (IIa) which ultimately can be transformed into the desired enantiomer (Ia) through an iterative process, thereby increasing overall yield of the process and reducing formation of waste material.

Process steps (v) and (vi) as described here above can be individually or collectively performed in batch mode or according to a continuous process, using for example microreactors.

The salt resolution of compounds of formula (IIa) with the chiral acids of formula (IV) according to the present invention is particularly advantageous as it allows obtention of compound of formula (Ia) with high enantiomeric excess and a high yield.

The term "Enantiomeric Excess" as used herein is generally expressed as percentage enantiomeric excess and refers to the amount of an enantiomer with respect to another and is calculated as follows % ee=[([A]−[B]):([A]+[B])]×100, where [A] is the concentration of one of the enantiomers, and [B] is the concentration of the other enantiomer.

Typical % ee of compounds of mineral salt of compound of formula (Ia) according to the present invention are comprised between 90 and 100%.

Enantiomeric excess of compounds according to the present invention are preferably at least 98%.

The term "diastereomeric Excess" as used herein is generally expressed as percentage diastereomeric excess and refers to the amount of a diastereoisomer with respect to another and is calculated as follows:

% de=[([A]−[B]):([A]+[B])]×100, where [A] is the concentration of one of the diastereoisomer, and [B] is the concentration of the other diastereoisomer.

Typical % de of compounds of formula (Va) according to the present invention are comprised between 80 and 100%.

Diastereosiomeric excess of compounds according to the present invention is preferably at least 90%.

The salt resolution according to the present invention is generally performed with a better Resolvability than the Resolvability that can be obtained with commonly employed chiral acids which are available at the industrial scale.

The term "Resolvability" as used herein measures the efficiency of a resolution process and is defined by Fogassy et al in J. Chem. Res (S) 11, 346 (1981) as follows.

The term Resolvability is represented by S and is defined as the product of the yield of the resolution reaction and the diastereosiomeric excess of the isolated salt:

S=y×de

Resolvability values according to the present invention are comprised between about 0.45 and about 0.90.

Furthermore, the salt resolution process according to the present invention requires less crystallization steps of compound of formula (Ia) to obtain the desired optical purity. Hence, yields and efficiency of the process are increased over those described in the prior art.

In a further embodiment, the present invention relates to the use of diastereoisomeric salts (Va) selected from the group consisting of (S)-1,2,3,4-tetrahydro-5-methoxy-N-propyl-naphthalen-2-ammonium (R)-2-methoxy-2-phenylacetate (Vaa), (S)-1,2,3,4-tetrahydro-5-methoxy-N-propyl-naphthalen-2-ammonium (R)-2-(2-chlorophenyl)-2-hydroxyacetate (Vab), (S)-1,2,3,4-tetrahydro-5-methoxy-N-propyl-naphthalen-2-ammonium (S)-2-hydroxy-3-phenylpropionate (Vac), (S)-1,2,3,4-tetrahydro-5-methoxy-N-propyl-naphthalen-2-ammonium (R) 2-(6-methoxy-2-naphthyl)-propionate (Vad), and (S)-1,2,3,4-tetrahydro-5-methoxy-N-propyl-naphthalen-2-ammonium (S)-2-(5-chloro-2-oxo-2,3-dihydroindol-1-yl)-propionate (Vah) as synthetic intermediates for the synthesis of rotigotine.

Use of said diastereoisomeric salts for the synthesis of rotigotine is particularly advantageous as such salts can be manufactured on a large scale. Moreover, their use allows obtention of the desired enantiomers of synthetic intermediates (I) with a high chiral purity while the undesired enantiomer is either easily removed from the reaction or can be easily recycled into the desired enantiomer.

Furthermore, the process according to the present invention affords compound of formula (Ia) which have a better quality/purity then when manufactured according to other processes.

Hence, the overall manufacturing process using diastereoisomeric salts of formula (Va) is a cost-effective and efficient alternative synthetic pathway to rotigotine.

Free base or salts of compounds of formula (Ia) obtained according to any aspect of the present invention may be further transformed into rotigotine as shown in the following scheme.

Scheme 8

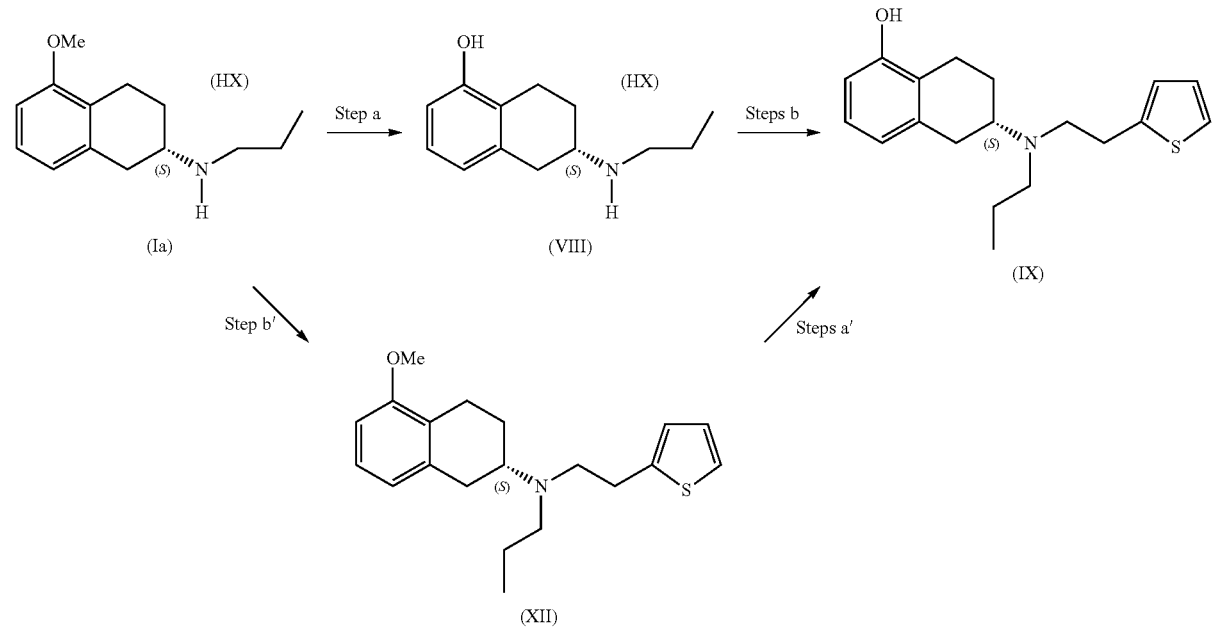

Delakylations such as steps a and a' of scheme 8 are generally well described in the literature and achieved by reaction with a strong mineral acid or derivative containing a nucleophilic counterion such as HBr or HI, or by reaction with a lewis acid such as BBr$_3$ or AlCl$_3$ and by reaction with a nucleophilic thiolate. Preferably these steps are performed by reaction with HBr with or without the presence of acetic acid.

Steps b and b' of scheme 10 are generally achieved by reacting compound of formula (Ia) or compound of formula (VIII) with 2-(2-thienyl)ethanolbenzenesulfonate or 2-(2-thienyl)ethanol toluenesulfonate in the presence of an alkali metal carbonate or an alkali metal bicarbonate.

The resulting salt of compound of formula (IX) is then transformed into the corresponding free base (IX) by reaction with a base according to methods known by the person skilled in the art.

In another embodiment according to the present invention, resolution is achieved by the differential separation method, more preferably by chiral chromatographic separation using columns packed with a chiral stationary phase (CSP) and a mobile phase. Chiral chromatographic separation may be carried out in batch or by Multi Column Chromatography (MCC).

The term batch as used herein refers to a discontinuous chromatographic separation technology based on controlled injections of a mixture onto a column packed with a stationary phase. The separated components of the mixture are then withdrawn at the outlet, alternating the collect of the two enantiomers from the system. This approach would include, but is not limited to, liquid chromatography using solvent or mixture of solvents or Supercritical Fluid Chromatography (SFC) using a substance in supercritical state with a co-solvent or a mixture of co-solvents.

"Supercritical state" as used herein when referring to a substance means that the substance is at a temperature and pressure above its critical point Hence, Supercritical Fluid Chromatography is a technique used for the enantiomeric resolution of racemic mixtures as described in the article "TRIAL SEPARATIONS and is recommended for preparative-scale separations of enantiomers" (Ann Thayer, C&EN Houston, Sep. 5, 2005, Volume 83, Number 36, pp. 49-53).

The term "Multi Column Chromatography" (MCC) as used herein refers to a continuous chromatographic separation technology based on the continuous controlled injection of mixtures onto a series of linked columns packed with a stationary phase. The separated components of the mixture are then withdrawn continuously from the system. This approach would include, but is not limited to, Simulated Moving Bed chromatography mode (SMB mode), or mode where the inlet and outlet ports are shifted asynchronously (such as the Varicol mode) or mode in which inlet and outlet flow rates and/or concentrations are changing in time during the switching period.

The application of the SMB technique for the enantiomeric resolution of racemic mixtures has, for example, been described in the article "Lit mobile simulé. Application à la séparation d'isomères optiques [Simulated mobile bed. Application to the separation of optical isomers]" by R. M. Nicoud, Information Chimie No. 368 (May 1995), pp. 113-115.

The Varicol system is described in international patent application WO 00/25885 and the mode in which fluid flow rates are changing in time during the switching period is described in U.S. Pat. No. 5,102,553.

Hence, in another embodiment according to the present invention, resolution of compound of formula (II) is performed by chiral chromatographic separation. In a further embodiment according to the present invention, resolution of compound of formula (II) is performed by MCC or SFC.

Compounds of formula (II) which are particularly suitable to undergo chiral chromatographic separation according to the present invention are compounds of formula (II) wherein R$^1$ and R$^2$ are alkyl and R$^3$ is an alkoxycarbonyl, alkylcarbonyl, aryloxycarbonyl or arylcarbonyl.

Hence, it is also an objective of the present invention to provide compounds of formula (II) wherein R$^1$ and R$^2$ are alkyl and R$^3$ is an alkoxycarbonyl, alkylcarbonyl, aryloxycarbonyl or arylcarbonyl.

In a particular embodiment according to the present invention, compounds of formula (II) which are particularly suitable to undergo chiral chromatographic separation according to the present invention are compounds of formula (II) wherein R$^1$ and R$^2$ are alkyl and R$^3$ is an alkoxycarbonyl.

Examples of such compounds of formula (II) are N-(methoxycarbamoyl)-N-propyl-5-Methoxy-2-aminotetralin, N-(ethoxycarbamoyl)-N-propyl-5-Methoxy-2-aminotetralin and N-(tert-butoxycarbamoyl)-N-propyl-5-Methoxy-2-aminotetralin, hereafter collectively referred to as compounds of formula (IIb).

Said compounds of formula (IIb) are particularly advantageous as they are surprisingly highly soluble in the mobile phase which makes them easier to handle when performing Chiral Chromatographic separation on preparative or industrial scale. Furthermore, the alkoxycarbonyl group may be removed easily so that compounds of formula (Ib) resulting from the chiral chromatographic separation of compounds of formula (IIb) may undergo further transformation, for example, into rotigotine.

Compounds of formula (II) wherein R$^1$ and R$^2$ are alkyl and R$^3$ is an alkoxycarbonyl may be obtained by reacting compounds of formula (II) wherein R$^1$ and R$^2$ are alkyl and R$^3$ is hydrogen with an alkylchloroformate in a solvent in the presence of a base.

In a particular embodiment, the present invention relates to a process of manufacture of substantially optically pure (S)—N-(alkoxycarbamoyl)-N-propyl-5-Methoxy-2-aminotetralin (Ib) comprising chiral chromatographic separation of N-(alkoxycarbamoyl)-N-propyl-5-Methoxy-2-aminotetralin (IIb), as shown in following scheme 9, wherein R$^a$ is a alkyl.

Scheme 9

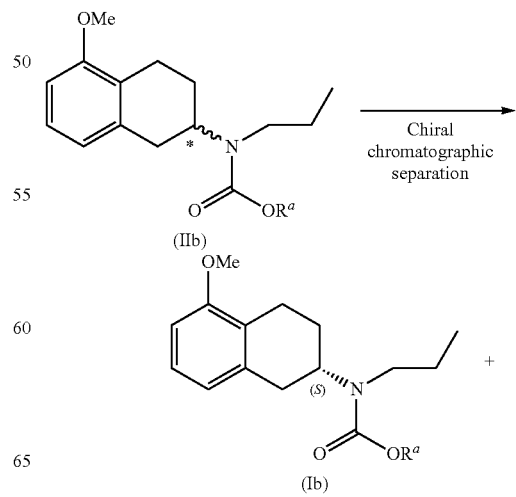

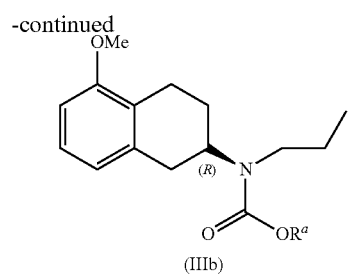

(IIIb)

In a particular embodiment according to the present invention, $R^a$ is a $C_{1-4}$ alkyl. Examples of $C_{1-4}$ alkyl are methyl, ethyl, isobutyl and tert-butyl.

In one further particular embodiment, the present invention relates to a process of manufacture of substantially optically pure (S)—N-(alkoxycarbamoyl)-N-propyl-5-Methoxy-2-aminotetralin (Ib) comprising MCC separation of N-(alkoxycarbamoyl)-N-propyl-5-Methoxy-2-aminotetralin (IIb).

In another further particular embodiment, the present invention relates to a process of manufacture of substantially optically pure (S)—N-(alkoxycarbamoyl)-N-propyl-5-Methoxy-2-aminotetralin (Ib) comprising supercritical fluid chromatographic separation of N-(alkoxycarbamoyl)-N-propyl-5-Methoxy-2-aminotetralin (IIb).

N-(alkoxycarbamoyl)-N-propyl-5-Methoxy-2-aminotetralin (IIb), wherein $R^a$ is a methyl, i.e. N-(methoxycarbamoyl)-N-propyl-5-Methoxy-2-aminotetralin, is particularly suitable for MCC or SFC chiral chromatographic separation.

N-(alkoxycarbamoyl)-N-propyl-5-Methoxy-2-aminotetralin (IIb) is more stable to air oxidation than free base of compound of formula (IIa), making it a more robust substrate for Chiral Chromatographic Separation.

Columns used according to the present invention are generally packed with a CSP which comprises a silica backbone onto which a polymeric chiral selector is coated according to techniques well-known in the art.

The polymeric chiral selector may additionally be immobilized onto the silica backbone which provides to the column, among other advantages, a better resistance to solvents.

The polymeric chiral selector according to the present invention generally comprises a polysaccharide, for example amylose or cellulose.

Examples of polymeric chiral selector which may be used according to the present invention are cellulose tris(4-methylbenzoate) (CHIRALCEL® OJ), cellulose tribenzoate (CHIRALCEL OB), amylose tris(3,5-dimethylphenylcarbamate) (CHIRALPAK® AD or CHIRALPAK® IA), cellulose tris(3,5-dimethylphenylcarbamate) (CHIRALCEL OD or CHIRALPAK® IB), cellulose tris(4-methylphenylcarbamate) (CHIRALCEL® OG), cellulose tris(3,5-dichlorophenylcarbamate) (CHIRALPAK® IC), amylose tris(3-chloro-4-methylphenylcarbamate) (CHIRALPAK® AZ), cellulose tris(3-chloro-4-methylphenylcarbamate) (CHIRALCEL® OZ or Lux™ Cellulose-2), amylose tris(5-chloro-2-methylphenylcarbamate) (CHIRALPAK® AY or Lux™ Amylose-2) and amylose tris(5-chloro-2-methylphenylcarbamate) (CHIRALPAK® AZ).

The chiral selector according to the present invention can also be a donor-acceptor phase, for example Pirkle-concept.

Example of such donor-acceptor phase which may be used according to the present invention are 1-(3,5-dinitrobenzamido)-1,2,3,4-tetrahydrophenanthrene (WHELK-O1).

In a particular embodiment, the present invention relates to a process of manufacture of (S)—N-(alkoxycarbamoyl)-N-propyl-5-Methoxy-2-aminotetralin (Ib) comprising chiral chromatographic separation of N-(alkoxycarbamoyl)-N-propyl-5-methoxy-2-aminotetralin (IIb) using cellulose tris(3,5-dimethylphenylcarbamate) coated onto a silica backbone as chiral stationary phase.

Examples of mobile phase that may be used for MCC separation according to the present invention are alkanes such as heptane, hexane, alcohols, such as methanol, ethanol, iso-propanol, n-propanol, acetonitrile and ethyl acetate. These solvents may be used alone or in combination one with another.

When mixtures of solvents are used, the ratio will depend upon the type of solvents constituting the mixture, upon the type of column which is used and upon the solubility in those mixtures of the compound to be separated.

Examples of mixtures of solvents according to the present invention are mixtures of alcohols or mixtures of alcohol with alkanes or mixtures of alcohol with acetonitrile or mixture of alcohol with ethyl acetate.

Examples of mobile phase that may be used for Supercritical Fluid Chromatographic separation according to the present invention are $CO_2$ in a supercritical state in combination with alcohols, such as methanol, ethanol, iso-propanol, n-propanol.

Supercritical state when referring to $CO_2$ means a fluid state of carbon dioxide where it is held at or above its critical temperature and critical pressure.

In general, according to the present invention $CO_2$ will be held in a fluid state above its critical temperature and critical pressure.

According to the present invention, a productivity of the chiral chromatographic separation greater than 1 Kg of racemic mixture separated per Kg of Chiral Stationary Phase per day can be achieved either by liquid or supercritical fluid chromatography.

(S)—N-(alkoxycarbamoyl)-N-propyl-5-Methoxy-2-aminotetralin (Ib) obtained according to this aspect of the invention is generally substantially optically pure. This is particularly advantageous as it avoids the use of iterative purification steps such as crystallization which could impact on the productivity of the overall process.

(R)—N-(alkoxycarbamoyl)-N-propyl-5-Methoxy-2-aminotetralin (IIIb) obtained according to this aspect of the invention is generally substantially optically pure.

N-(alkoxycarbamoyl)-N-propyl-5-Methoxy-2-aminotetralin (IIb), are synthetized by reaction of the free base (IIa') generated in advance or in situ by reaction of compound of formula (IIa), under basic conditions with the corresponding chloroformate or anhydride, according to methods known by those skilled in the art, and as shown in scheme below.

Scheme 10

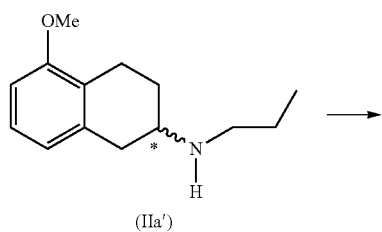

(IIa')

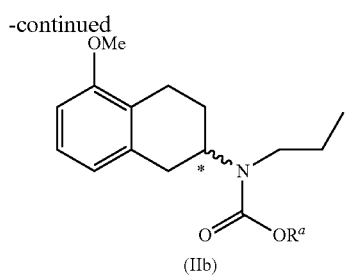

(IIb)

Compounds of formula (Ib) obtained according to the present invention may be further transformed into rotigotine as shown in the following scheme.

Use of such compounds is particular advantageous as commercially available Chiral Stationary Phases do not allow chiral separation of 5,6,7,8-tetrahydro-6-[propyl-[2-(2-thienyl)ethyl]-amino]-1-naphthalenol by MCC.

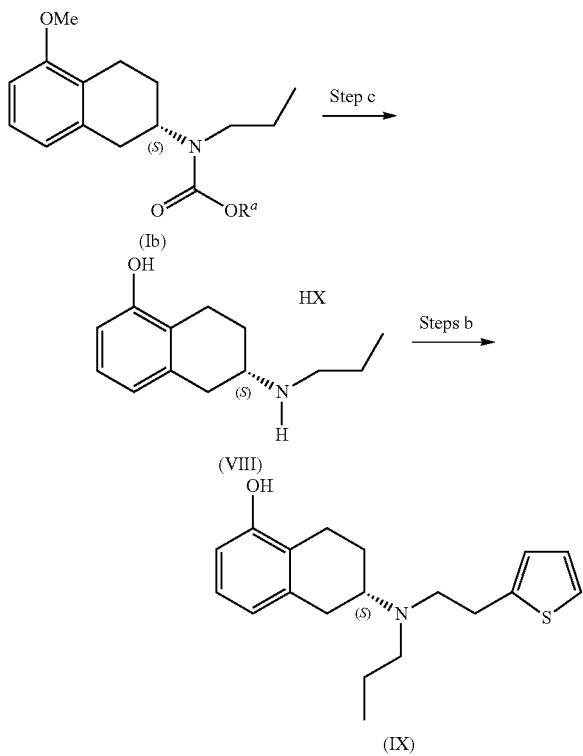

Step c of scheme 11 is generally achieved by reacting compound of formula (Ib) with acidic demethylating agents such as concentrated HBr.

Alternatively compounds of formula (Ib) may react with a mineral acid as defined here above to afford compounds of formula (Ia) which are further transformed into rotigotine as shown in scheme 8.

Steps a, b, c may also be performed according to any method known to the persons skilled in the art.

Compounds of formula (IX) may be obtained in free or salt form.

Salts of compounds of formula (IX) are preferably hydrochloride or hydrobromide salt.

Hence, the present invention also relates to the use of synthetic intermediates (Ia) and (Ib) obtained according to schemes 6 or 9 for the synthesis of N-substituted aminotetralins. In particular, synthetic intermediates (Ia) and (Ib) obtained according to schemes 6 or 9, are useful for the synthesis of rotigotine and salts thereof.

It is or will be understood that variations and modifications, including telescoping of certain process steps (i.e. an intermediate is not isolated but processed directly into another chemical intermediate or another physical form or phase), according to the present invention, can be affected without departing from the scope or spirit of the invention.

EXAMPLES

1HNMR spectra were measured on a Varian 400 MHz and 300 MHz and Varian 400 MHz spectrometer in deuterosolvents with TMS as an internal standard at room temperature.

$^1$H NMR data were reported in the order of chemical shift, multiplicity (s, singlet; d, doublet; t, triplet; q, quartet; m, multiplet; app, apparent and/or multiple resonance), coupling constant (J) in hertz (Hz) and number of protons.

High Performance Liquid Chromatography (HPLC) spectra are recorded on an Alliance Waters 2695 equipped with the HPLC spectra were recorded on an Alliance Waters 2695 equipped with an Atlantis T3 3 microns column (4.6×100 mm), detecting at 200 nm—starting solvent composition=water:90% vol/water+1% $H_3PO_4$:10% vol; final solvent composition=water+1% $H_3PO_4$:10% vol/acetonitrile:90% vol in 6 minutes followed by re-equilibration period of 1 min to the initial solvent composition.

Chiral HPLC are recorded on a Alliance Waters 2695 equipped with a Chiralpak AD-H® 5 μm (250×4.6 mm) column with detection at 229 nm Mass spectra were recorded on waters 3100 triple quadrapole spectrometer. IR spectra were recorded with a Nicolet 380 FT-IR (neat for liquids and KBr pellets for solids).

HPLC was analyzed on different systems Waters 2695 PDA, Agilent 1100 UV, Shimadzu-SCL-IOAVP.

The HPLC data were reported in area %.

Melting point was recorded on Polmon moeld No. MP96.

MCC used is based on 8*48 model with 2 pumps and internal recycling loop, able to be operated with synchronous or asynchronous shift and equipped with an online HPLC (Agilent 1100) on board.

SFC data were recorded on an analytical PIC-SFC system equipped with DAD and preparative separation done on a SFC-PIClab600 system, used with 50 mm SFC column from PIC solution.

Example 1

Preparation of (S)-1,2,3,4-tetrahydro-5-methoxy-N-propyl-naphthalen-2-amine hydrochloride (IIa)

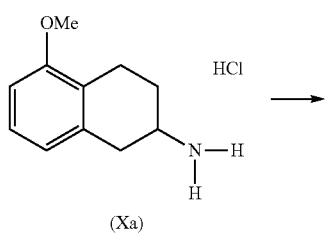

(Xa)

-continued

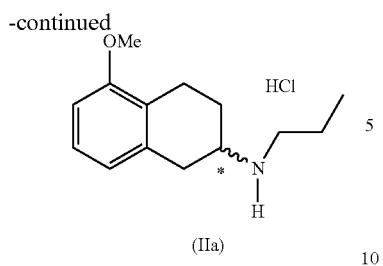

(IIa)

-continued

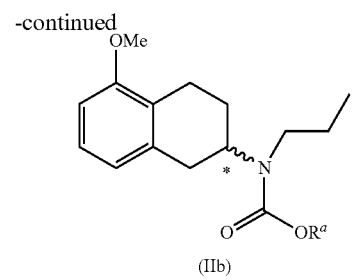

(IIb)

A 2 L reactor with double jacket temperature control was charged with 5-methoxy-2-aminotetraline hydrochloride (Xa) (161 g), sodium acetate (62 g), and tetrahydrofuran (750 mL). The suspension was stirred at 0° C. To that suspension were added glacial acetic acid (22 mL), sodium triacetoxyborohydride (200 g) and propionalhedyde (XIa) (48 g diluted with 50 mL of tetrahydrofuran via a dropping funnel maintaining the mass temperature below 10° C. The resulting suspension was stirred overnight at 0° C. To that suspension was slowly added a 25% solution of sodium hydroxide (250 mL) at 0° C. and the resulting mixture was let to warm up to room temperature under stirring for 30 minutes. The aqueous layer was discarded and the organic layer was washed with a 6.25% solution of sodium hydroxide (200 mL). The aqueous layer was discarded and the organic layer was heated at 50° C. To this solution concentrated hydrochloric acid (77 mL) was added over 20 minutes and the resulting thick suspension was diluted with 150 mL of tetrahydrofuran. The suspension is maintained at 50° C. for 30 minutes then rapidly cooled to 10° C. and stirred at 10° C. for 30 minutes. The product was isolated by filtration, washed 2 times with cold THF (2×200 mL) and dried under vacuum at 40° C. until constant weight to give N-Propyl MAT.HCl salt as an white solid with 78% yield.

NMR 1H (dmso d6) δ (ppm): 0.94 (3H, d), 1.76 (3H, m), 2.04 (1H, m), 2.32 (1H, m), 2.47 (1H, m), 2.99 (2H, m), 3.17 (1H, m), 3.30 (1H, dd), 3.76 (3H, s), 3.86 (1H, m), 5.65 (2H, t), 6.71 (1H, d), 6.79 (1H, d), 7.12 (1H, t), 9.15 (2H, broad d) LC-MS ES+220.2, 161.1

Example 2

Preparation of N-(alkoxycarbamoyl)-N-propyl-5-Methoxy-2-aminotetralin (IIb)

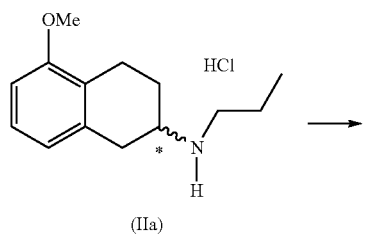

(IIa)

Example 2a

Preparation of N-(methoxycarbamoyl)-N-propyl-5-Methoxy-2-aminotetralin (Compound (IIb) Wherein $R^a$ is methyl)

N-propyl-5-methoxy-2-aminotetralin hydrochloride (IIa) was suspended in dichloromethane (10 vol). Triethylamine (1.64 vol, 3 eq) and methyl chloroformate (0.36 vol, 1.2 eq) were added. Additional methyl chloroformate (0.13 vol) was added. The mixture stirred at ambient temperature over 24 h. Product isolated by extraction and purified by acidic and neutral aqueous washes. Organic layer dried over magnesium sulfate and solvent evaporated to give a clear oil. Product obtained in 85% yield and 100% HPLC conversion.

1H NMR (DMSO) δ 7.05-7.11 (1H, t, ArH), 6.72-6.77 (1H, d, ArH), 6.65-6.69 (1H, d, ArH), 3.92-4.05 (1H, br s, CH), 3.75 (3H, s, OMe), 3.59 (3H, s, OMe), 3.44 (1H, s, CH), 3.05-3.15 (2H, m, CH2), 2.84-2.99 (2H, m, CH2), 2.65-2.75 (2H, m, CH2), 2.83-2.91 (2H, m, CH2), 1.45-1.58 (2H, m, CH2) and 0.80-0.87 (3H, m, CH3). TOF MS ES+278.1998 [M+1] IR (cm$^{-1}$) 3485.13, 2957.72, 1693.42, 1586.48, 1468.64, 1437.92

Example 2b

Preparation of N-(ethoxycarbamoyl)-N-propyl-5-Methoxy-2-aminotetralin (Compound (IIb) Wherein $R^a$ is ethyl)

N-propyl-5-methoxy-2-aminotetralin hydrochloride (IIa) (1 wt) was suspended in dichloromethane (10 vol). Triethylamine (1.64 vol, 3 eq) and ethyl chloroformate (0.44 vol, 1.2 eq) were added. The mixture was stirred at ambient temperature over 24 h. Additional ethyl chloroformate (0.07 vol, 0.2 eq.) was added. Product isolated by extraction and purified by acidic and neutral aqueous washes. Organic layer dried over sodium sulfate and the solvent evaporated. Product obtained in 88% yield and 100% purity as a reddish oil.

$^1$H NMR δ 7.05-7.09 (1H, t, ArH), 6.74-6.76 (1H, d, ArH), 6.65-6.67 (1H, d, ArH), 3.90-4.10 (3H, m), 3.73 (3H, s, OMe), 3.05-3.13 (2H, m, CH$_2$), 2.83-2.98 (2H, m, CH2), 2.65-2.73 (2H, m, CH$_2$), 1.76-1.92 (1H, m, CH2), 1.57-1.67 (2H, m, CH$_2$), 1.14-1.18 (3H, m, CH$_3$) and 0.80-0.84 (3H, m, CH$_3$).

Example 2c

Preparation of N-(tert-butoxycarbamoyl)-N-propyl-5-Methoxy-2-aminotetralin (Compound (IIb) Wherein $R^a$ is tert-butyl)

N-propyl-5-methoxy-2-aminotetralin hydrochloride (IIa) (1 wt) was suspended in a mixture of THF:H$_2$O (1:1) (10 vol).

NaHCO$_3$ (0.98 wt) and Boc$_2$O (1.02 wt) were added. The mixture was stirred from 0° C. to ambient temperature over 20 h. Product isolated by extraction and purified by aqueous washes. Organic layer dried over magnesium sulphate and solvent evaporated. Product obtained in 78% yield and 96.3% purity.

$^1$H NMR δ 7.06-7.14 (1H, m, ArH), 6.63-6.76 (2H, m, ArH), 3.83 (3H, s, OMe), 2.78-3.25 (5H, m, CH, CH$_2$), 2.54-2.67 (1H, m, CH2), 1.97-2.07 (1H, m, CH$_2$), 1.76-1.92 (1H, m, CH2), 1.57-1.67 (2H, m, CH$_2$), 1.49 (9H, s, nu), 1.24-1.34 (1H, m, CH$_2$) and 0.86-0.83 (3H, m, CH3).

Example 3

Preparation of 1,2,3,4-tetrahydro-5-methoxy-N-propyl-naphthalen-2-amine (IIa') from 1,2,3,4-tetrahydro-5-methoxy-N-propyl-naphthalen-2-amine hydrochloride (IIa)

Method A 22 g of (IIa) salt were suspended in a mixture of MTBE (110 mL) and aqueous sodium hydroxide (4 g in 110 mL of deionised water). The resulting suspension was stirred at room temperature until 2 homogeneous layers were obtained. The layers were separated and the aqueous layer was extracted with 100 mL of MTBE. The organic layers were combined, washed with 100 mL of deionised water, then dried over magnesium sulfate. After filtration of the solid, MTBE was evaporated to yield 18 g of 1,2,3,4-tetrahydro-5-methoxy-N-propyl-naphthalen-2-amine (IIa') as a colourless oil (yield: 95%).

NMR $^1$H (CDCl$_3$) d (ppm): 0.96 (3H, d), 1.54 (3H, q), 2.07 (1H, m), 2.59 (2H, q), 2.69 (2H, t), 2.90 (2H, m), 3.01 (2H, dd), 3.80 (3H, s), 6.65 (1H, d), 6.71 (1H, d), 7.09 (1H, t).

Method B 15 g of (IIa) salt and 32 g of potassium carbonate were suspended in 75 g of MeTHF. The resulting suspension was stirred at the reflux temperature of MeTHF overnight. After cooling to room temperature, the suspension was filtered and the solid was discarded. The filtrate was evaporated to yield 13 g of 1,2,3,4-tetrahydro-5-methoxy-N-propyl-naphthalen-2-amine (IIa') as a colourless oil (yield: 98%).

Example 4

Preparation of Diastereoisomeric Salts of Formula (Va)

Example 4a

Preparation of (S)-1,2,3,4-tetrahydro-5-methoxy-N-propyl-naphthalen-2-ammonium-(R)-2-methoxy-2-phenylacetate (Vaa) in Methanol A portion of 1.1 g of (R)-2-methoxy-2-phenylacetic acid (IVa) was added to a solution of 2 g of (IIa') in solution in 35 mL of methanol at 25° C. The obtained suspension was kept under stirring at 25° C. overnight. The solid collected by filtration was rinsed with 1 mL of methanol to give 1 g of (S)-1,2,3,4-tetrahydro-5-methoxy-N-propyl-naphthalen-2-ammonium-(R)-2-methoxy-2-phenylacetate (Vaa) (yield: 29%; chiral HPLC: 95% of (Vaa); 5% (R)-1,2,3,4-tetrahydro-5-methoxy-N-propyl-naphthalen-2-ammonium-(R)-2-methoxy-2-phenylacetate (V'aa).

NMR 1H (dmso-d6) δ (ppm): 0.89 (3H, d), 1.50 (3H, m), 2.18 (1H, m), 2.47 (1H, m), 2.84 (4H, m), 3.22 (1H, m), 3.27 (1H, s), 3.76 (3H, s), 4.55 (1H, s), 6.66 (1H, d), 6.77 (1H, d), 7.08 (1H, t), 7.30 (2H, m), 7.36 (2H, m).

Example 4b

Preparation of (S)-1,2,3,4-tetrahydro-5-methoxy-N-propyl-naphthalen-2-ammonium-(R)-2-methoxy-2-phenylacetate (Vaa) in Methanol-Water (1:1)

A portion of 1.1 g of (R)-2-methoxy-2-phenylacetic acid (IVa) was added to a solution of 2 g of (IIa') in solution in 20 mL of methanol-water (1:1) at room temperature. The resulting mixture turned into a thick suspension. The obtained suspension was heated at 60° C. then cooled to 25° C. and kept under stirring at this temperature overnight. The solid collected by filtration was rinsed with 1 mL of methanol-water (1:1), slurried in 20 mL of methanol-water (1:1) at 60° C., and cooled at 25° C. The slurry was filtered, and the collected solid was rinsed with 1 mL of methanol-water (1:1), then vacuum dried to give 1.5 g of (S)-1,2,3,4-tetrahydro-5-methoxy-N-propyl-naphthalen-2-ammonium-(R)-2-methoxy-2-phenylacetate (Vaa) (yield: 42%; chiral HPLC: 96.5% of (Vaa); 3.5% (R)-1,2,3,4-tetrahydro-5-methoxy-N-propyl-naphthalen-2-ammonium-(R)-2-methoxy-2-phenylacetate (V'aa).

NMR $^1$H (dmso d6) δ (ppm): 0.89 (3H, d), 1.50 (3H, m), 2.18 (1H, m), 2.47 (1H, m), 2.84 (4H, m), 3.22 (1H, m), 3.27 (1H, s), 3.76 (3H, s), 4.55 (1H, s), 6.66 (1H, d), 6.77 (1H, d), 7.08 (1H, t), 7.30 (2H, m), 7.36 (2H, m).

Example 4c

Preparation of (S)-1,2,3,4-tetrahydro-5-methoxy-N-propyl-naphthalen-2-ammonium (R)-2-(2-chlorophenyl)-2-hydroxyacetate (Vab) in Ethanol A portion of 0.85 g of (R)-2-(2-chlorophenyl)-2-hydroxyacetic acid (IVb) was added to a solution of 1 g of (IIa') in a solution in 5 mL of absolute ethanol. The resulting mixture was refluxed then cooled to 35° C. The resulting solid was filtered, rinsed with 2 mL of ethanol and dried in a vacuum oven to give 0.31 g of (S)-1,2,3,4-tetrahydro-5-methoxy-N-propyl-naphthalen-2-ammonium (R)-2-(2-chlorophenyl)-2-hydroxyacetate (Vab) (yield: 17%; chiral HPLC 96.8% of (Vb); 3.2% of (R)-1,2,3,4-tetrahydro-5-methoxy-N-propyl-naphthalen-2-ammonium (R)-2-(2-chlorophenyl)-2-hydroxyacetate (V'ab).

NMR $^1$H (dmso d6) δ (ppm): 0.88 (3H, d), 1.54 (3H, m), 2.18 (1H, m), 2.47 (1H, m), 2.84 (4H, m), 3.22 (1H, m), 3.76 (3H, s), 4.96 (1H, s), 6.66 (1H, d), 6.77 (1H, d), 7.11 (1H, t), 7.19 (1H, m), 7.33 (2H, m).

Example 4d

Preparation of (S)-1,2,3,4-tetrahydro-5-methoxy-N-propyl-naphthalen-2-ammonium (R)-2-(2-chlorophenyl)-2-hydroxyacetate (Vab) in Ethyl acetate A portion of 0.85 g of (R)-2-(2-chlorophenyl)-2-hydroxyacetic acid (IVb) was added to a solution of 1.0 g of (IIa') in a solution of 5 mL of ethyl acetate. The resulting mixture was refluxed until a clear solution was obtained, then let to cool to 50° C. The resulting solid was filtered, rinsed twice with 2 mL of ethyl acetate and dried in a vacuum oven to give 0.45 g of (S)-1,2,3,4-tetrahydro-5-methoxy-N-propyl-naphthalen-2-ammonium (R)-2-(2-chlorophenyl)-2-hydroxyacetate in Ethyl acetate (Vab) (yield: 30.6%; chiral HPLC: 96.1% of (Vab); 3.9% of (R)-1,2,3,4-tetrahydro-5-methoxy-N-propyl-naphthalen-2-ammonium (R)-2-(2-chlorophenyl)-2-hydroxyacetate (V'ab))

NMR 1H (dmso d6) δ (ppm): 0.88 (3H, d), 1.54 (3H, m), 2.18 (1H, m), 2.47 (1H, m), 2.84 (4H, m), 3.22 (1H, m), 3.76 (3H, s), 4.96 (1H, s), 6.66 (1H, d), 6.77 (1H, d), 7.11 (1H, t), 7.19 (1H, m), 7.33 (2H, m).

Melting point—DSC: 134.0° C. (onset)

Example 4e

Preparation of (S)-1,2,3,4-tetrahydro-5-methoxy-N-propyl-naphthalen-2-ammonium (R)-2-(2-chlorophenyl)-2-hydroxyacetate (Vab) in Me-Tetrahydrofuran A portion of 2.1 g of (R)-2-(2-chlorophenyl)-2-hydroxy-acetic acid (IVb) was added to a solution of 2.5 g of (IIa') in solution in 10 mL of methyl-THF. The resulting mixture was heated to 75° C. until a clear solution was obtained, then cooled to room temperature. The resulting solid was filtered, rinsed twice with 5 mL of methyl-THF and dried in a vacuum oven to give 1.1 g of (S)-1,2,3,4-tetrahydro-5-methoxy-N-propyl-naphthalen-2-ammonium (R)-2-(2-chlorophenyl)-2-hydroxyacetate (Vab) (yield: 24.7%; chiral HPLC: 97.9% of (Vab); 2.1% of (R)-1,2,3,4-tetrahydro-5-methoxy-N-propyl-naphthalen-2-ammonium (R)-2-(2-chlorophenyl)-2-hydroxyacetate (V'ab)).

NMR $^1$H (dmso d6) δ (ppm): 0.88 (3H, d), 1.54 (3H, m), 2.18 (1H, m), 2.47 (1H, m), 2.84 (4H, m), 3.22 (1H, m), 3.76 (3H, s), 4.96 (1H, s), 6.66 (1H, d), 6.77 (1H, d), 7.11 (1H, t), 7.19 (1H, m), 7.33 (2H, m).

Melting point—DSC: 136.3° C. (onset)

Example 4f

Preparation of (S)-1,2,3,4-tetrahydro-5-methoxy-N-propyl-naphthalen-2-ammonium (R)-2-(2-chlorophenyl)-2-hydroxyacetate (Vab) in Ethyl Acetate (AcOEt)

136 g of triethylamine were added to 250 g of (IIa) salt suspended in a mixture of water (750 mL) and of AcOEt (1000 mL). The resulting mixture was refluxed for 45 minutes. After cooling at 10° C., the layers were separated and the aqueous layer was discarded. The organic layer was washed twice with 500 mL of water, then azeotropically dried at constant volume. The resulting solution of (IIa'a) was then cooled to 55-60° C. and a portion of 183 g of (R)-2-(2-chlorophenyl)-2-hydroxyacetic acid (IVb) was added. The crystallisation was initiated by seeding with 2.5 g of substantially optically pure (Vab). The resulting suspension was stirred at 50° for 4 hours then cooled to 0° C. in 50° C. The solid was isolated by filtration, rinsed twice with 250 mL of AcOEt. The solid was slurried 720 mL of AcOEt; the slurry suspension was refluxed for 2 hours then cooled to 0° C. in 4 hours to be filtered. The isolated solid was rinsed with 300 mL of AcOEt and dried under vacuum to give 136 g of (S)-1,2,3,4-tetrahydro-5-methoxy-N-propyl-naphthalen-2-ammonium (R)-2-(2-chlorophenyl)-2-hydroxyacetate (Vab) (yield: 34%; chiral HPLC: 99.4% of (Vab); 0.6% of (R)-1,2,3,4-tetrahydro-5-methoxy-N-propyl-naphthalen-2-ammonium (R)-2-(2-chlorophenyl)-2-hydroxyacetate (V'ab)).

NMR $^1$H (dmso d6) δ (ppm): 0.88 (3H, d), 1.54 (3H, m), 2.18 (1H, m), 2.47 (1H, m), 2.84 (4H, m), 3.22 (1H, m), 3.76 (3H, s), 4.96 (1H, s), 6.66 (1H, d), 6.77 (1H, d), 7.11 (1H, t), 7.19 (1H, m), 7.33 (2H, m).

Example 4g

Preparation of (S)-1,2,3,4-tetrahydro-5-methoxy-N-propyl-naphthalen-2-ammonium (S)-2-hydroxy-3-phenylpropionate (Vac) in Isopropanol A portion of 0.38 g of (S)-2-hydroxy-3-phenylpropionic acid (IVc) was added to a solution of 1 g of (IIa') in solution in 5 mL of isopropanol. The resulting mixture was refluxed and cooled to 25° C. The suspension was diluted with 1 mL of isopropanol prior its filtration; the resulting solid was rinsed three times with 2 mL of isopropanol and dried in a vacuum oven to give 0.59 g of (S)-1,2,3,4-tetrahydro-5-methoxy-N-propyl-naphthalen-2-ammonium (S)-2-hydroxy-3-phenylpropionate (Vac) (yield: 34%; chiral HPLC: 95.2% of (Vac); 4.8% of 1,2,3,4-tetrahydro-5-methoxy-N-propyl-naphthalen-2-ammonium (S)-2-hydroxy-3-phenylpropionate (V'ac)).

NMR 1H (dmso d6) δ (ppm): 0.93 (3H, d), 1.65 (3H, m), 2.22 (1H, m), 2.48 (1H, m), 2.66 (1H, m), 2.84 (4H, m), 3.00 (1H, dd), 3.10 (1H, dd), 3.23 (1H, m), 3.76 (3H, s), 3.86 (1H, m), 6.69 (1H, d), 6.77 (1H, d), 7.11 (1H, t), 7.21 (5H, m)

Melting point—DSC 118.5° C. (onset)

Example 4h

Preparation of (S)-1,2,3,4-tetrahydro-5-methoxy-N-propyl-naphthalen-2-ammonium (S)-2-hydroxy-3-phenylpropionate (Vac) in THF A portion of 0.38 g of (S)-2-hydroxy-3-phenylpropionic acid (IVc) was added to a solution of 1 g of (IIa') in solution in 5 mL of THF. The resulting mixture was refluxed and cooled to 25° C. The solid obtained was filtered, rinsed three times with 2 mL of THF and dried in a vacuum oven to give 0.72 g of (S)-1,2,3,4-tetrahydro-5-methoxy-N-propyl-naphthalen-2-ammonium (S)-2-hydroxy-3-phenylpropionate (Vc) (yield: 41%; chiral HPLC: 91.4% of (Vac); 8.6% of (R)-1,2,3,4-tetrahydro-5-methoxy-N-propyl-naphthalen-2-ammonium (S)-2-hydroxy-3-phenylpropionate (Vac).

NMR 1H (dmso d6) δ (ppm): 0.93 (3H, d), 1.65 (3H, m), 2.22 (1H, m), 2.48 (1H, m), 2.66 (1H, m), 2.84 (4H, m), 3.00 (1H, dd), 3.10 (1H, dd), 3.23 (1H, m), 3.76 (3H, s), 3.86 (1H, m), 6.69 (1H, d), 6.77 (1H, d), 7.11 (1H, t), 7.21 (5H, m)

Melting point—DSC 111.9° C. (onset)

Example 4l

Preparation of (S)-1,2,3,4-tetrahydro-5-methoxy-N-propyl-naphthalen-2-ammonium (S)-2-hydroxy-3-phenylpropionate (Vac) in THF A portion of 2.3 g of (S)-2-hydroxy-3-phenylpropionic acid (IVc) was added to a solution of 6 g of (IIa') in solution in 60 mL of THF. The resulting mixture was refluxed and cooled to 20° C. in 10 hours. The solid formed was filtered, rinsed twice with 6 mL of THF and oven dried to give 4.8 g of (S)-1,2,3,4-tetrahydro-5-methoxy-N-propyl-naphthalen-2-ammonium (S)-2-hydroxy-3-phenylpropionate (Vac) (chiral HPLC: 80.2% of (Vc); 19.8% of (R)-1,2,3,4-tetrahydro-5-methoxy-N-propyl-naphthalen-2-ammonium (S)-2-hydroxy-3-phenylpropionate (V'ac))

4.7 g of (Vac) were suspended into 75 mL of tetrahydrofuran. The resulting suspension was refluxed until a slightly cloudy solution could be observed and then cooled to 5° C. The solid obtained upon cooling was filtered, rinsed twice with 5 mL of fresh THF and dried in a vacuum oven to give 4 g of (S)-1,2,3,4-tetrahydro-5-methoxy-N-propyl-naphthalen-2-ammonium (S)-2-hydroxy-3-phenylpropionate (Vac) (overall yield: 38%; chiral HPLC: 98.7% of (Vac); 1.3% of (R)-1,2,3,4-tetrahydro-5-methoxy-N-propyl-naphthalen-2-ammonium (S)-2-hydroxy-3-phenylpropionate (V'ac)).

NMR 1H (dmso d6) δ (ppm): 0.93 (3H, d), 1.65 (3H, m), 2.22 (1H, m), 2.48 (1H, m), 2.66 (1H, m), 2.84 (4H, m), 3.00 (1H, dd), 3.10 (1H, dd), 3.23 (1H, m), 3.76 (3H, s), 3.86 (1H, m), 6.69 (1H, d), 6.77 (1H, d), 7.11 (1H, t), 7.21 (5H, m)

Melting point—DSC 121.2° C. (onset)

Example 41

Preparation of (S)-1,2,3,4-tetrahydro-5-methoxy-N-propyl-naphthalen-2-ammonium (S)-2-hydroxy-3-phenylpropionate (Vac) in 2-methyl THF A solution of 60 g of (S)-2-hydroxy-3-phenylpropionic acid (IVc) in 365 mL of was added to a solution of 143 g of (IIa') in solution in 360 mL of Me-THF. The resulting suspension was stirred at 70° C. for 1 hour, then it was cooled to 25° C. in 7.5 hours and aged at 25° C. for 8 h. The solid was collected by filtration, rinsed twice with 70 mL of Me-THF and oven dried to give 113 g of (S)-1,2,3,4-tetrahydro-5-methoxy-N-propyl-naphthalen-2-ammonium (S)-2-hydroxy-3-phenylpropionate (Vac) (yield: 45%; chiral HPLC: 98.7% of (Vac); 1.3% of (R)-1,2,3,4-tetrahydro-5-methoxy-N-propyl-naphthalen-2-ammonium (S)-2-hydroxy-3-phenylpropionate (V'ac)).

NMR 1H (dmso d6) δ (ppm): 0.93 (3H, d), 1.65 (3H, m), 2.22 (1H, m), 2.48 (1H, m), 2.66 (1H, m), 2.84 (4H, m), 3.00 (1H, dd), 3.10 (1H, dd), 3.23 (1H, m), 3.76 (3H, s), 3.86 (1H, m), 6.69 (1H, d), 6.77 (1H, d), 7.11 (1H, t), 7.21 (5H, m)

Example 5

Preparation of Substantially Optically Pure ((S)-1,2,3,4-tetrahydro-5-methoxy-N-propyl-naphthalen-2-ammonium hydrochloride (Ia) from Salts (Va) Described in the Above Examples Example 5a Preparation of Substantially Optically Pure ((S)-1,2,3,4-tetrahydro-5-methoxy-N-propyl-naphthalen-2-ammonium hydrochloride (Ia) from Salt (Vac)

The isolated diastereomeric salt (S)-1,2,3,4-tetrahydro-5-methoxy-N-propyl-naphthalen-2-ammonium (S)-2-hydroxy-3-phenylpropionate (Vac) was suspended into a mixture of Me-THF (5 vol) and water (2 vol). Sodium hydroxide (1.1 eq) was added as a solid. The resulting suspension was stirred at room temperature until complete solubilisation. The layers were let to settle and the aqueous layer was discarded. The organic layer was washed twice with deionised water (2 vol), then heated at 60° C. (Ia) was formed by addition of a 37% solution of hydrochloric acid (1.1 eq.). After cooling at 0-10° C., the resulting solid was filtered, washed twice with Me-THF and dried under vacuum to afford (S)-1,2,3,4-tetrahydro-5-methoxy-N-propyl-naphthalen-2-amine hydrochloride (Ia) in (yield: 84%; chiral HPLC: 100% of (Ia)).

NMR 1H (dmso d6) δ (ppm): 0.94 (3H, d), 1.76 (3H, m), 2.04 (1H, m), 2.32 (1H, m), 2.47 (1H, m), 2.99 (2H, m), 3.17 (1H, m), 3.30 (1H, dd), 3.76 (3H, s), 3.86 (1H, m), 5.65 (2H, t), 6.71 (1H, d), 6.79 (1H, d), 7.12 (1H, t), 9.15 (2H, broad d)

Melting point—DSC: 282° C. (onset)

Example 5b

Preparation of ((S)-1,2,3,4-tetrahydro-5-methoxy-N-propyl-naphthalen-2-ammonium hydrochloride (Ia) from Salt (Vab)

The isolated diastereomeric salt (Vab) was suspended into a mixture of THF (5 vol) and water (1 vol). The resulting suspension was heated to 65° C. so that a clear solution was obtained. A 37% solution of hydrochloric acid (1.1 eq) was added over 15 minutes, the crystallisation of Ia starting after the addition of about one third of the acid. The resulting suspension was refluxed for 1 hour, then cooled to 60° C. and kept at this temperature for 1 hour, and finally then cooled to 0° C. in 6 hours. The resulting solid was filtered, washed twice with THF (1 vol) and dried under vacuum to afford (S)-1,2,3,4-tetrahydro-5-methoxy-N-propyl-naphthalen-2-amine hydrochloride (Ia) (yield: 94%; chiral HPLC: 100% of (Ia)).

NMR 1H (dmso d6) δ (ppm): 0.94 (3H, d), 1.76 (3H, m), 2.04 (1H, m), 2.32 (1H, m), 2.47 (1H, m), 2.99 (2H, m), 3.17 (1H, m), 3.30 (1H, dd), 3.76 (3H, s), 3.86 (1H, m), 5.65 (2H, t), 6.71 (1H, d), 6.79 (1H, d), 7.12 (1H, t), 9.15 (2H, broad d)

Example 6

Preparation of (S)-1,2,3,4-tetrahydro-5-methoxy-N-propyl-naphthalen-2-amine hydrochloride (Ia) Via the Isolation of (S)-(1,2,3,4-tetrahydro-5-methoxy-N-propyl-naphthalen-2-ammonium-(S)-2-methoxy-2-phenylacetate in the Mother Liquors of the Resolution of (IIa) with (S)-2-methoxy-2-phenylacetate A portion of 3.4 g of (S)-2-methoxy-2-phenylacetic acid (IVa') was added to a solution of 4 g of (IIa') in solution in 25 mL of methanol and 25 mL of water. The resulting suspension was refluxed, cooled to 25° C. then filtered to afford a solution of mother liquors containing (S)-1,2,3,4-tetrahydro-5-methoxy-N-propyl-naphthalen-2-ammonium-(S)-2-methoxy-2-phenylacetate (chiral HPLC: 98.04% of (Vaa'); 1.96% of (R)-1,2,3,4-tetrahydro-5-methoxy-N-propyl-naphthalen-2-ammonium (S)-2-methoxy-2-phenylacetate (V'aa').

The solution obtained from the mother liquors was evaporated to dryness by distillation. The residue obtained was diluted with 10 mL of THF and heated to 70° C. A solution of hydrochloric acid (2 equivalents) was added and a solid precipitated. The solid formed was isolated by filtration, rinsed with THF (2×1 mL) and dried under vacuum to give 1.8 g of (S)-1,2,3,4-tetrahydro-5-methoxy-N-propyl-naphthalen-2-amine hydrochloride (Ia) (overall yield from IIa': 38.5%; chiral HPLC: 99.7% of (Ia)).

NMR 1H (dmso d6) δ (ppm): 0.94 (3H, d), 1.76 (3H, m), 2.04 (1H, m), 2.32 (1H, m), 2.47 (1H, m), 2.99 (2H, m), 3.17 (1H, m), 3.30 (1H, dd), 3.76 (3H, s), 3.86 (1H, m), 5.65 (2H, t), 6.71 (1H, d), 6.79 (1H, d), 7.12 (1H, t), 9.15 (2H, broad d).

Example 7

Preparation of (RS)-1,2,3,4-tetrahydro-5-methoxy-N-propyl-naphthalen-2-amine hydrochloride (IIa) from Diastereoisomerically Salt (V'a)

7.1. Preparation of (R)-1,2,3,4-tetrahydro-5-methoxy-N-propyl-naphthalen-2-amine (III)

To a stirred solution of 1 equivalent of any of the undesired diastereoisomeric salt (V'a) described in example 5, is added water (3 vol vs 1,2,3,4-tetrahydro-5-methoxy-N-propyl-naphthalen-2-amine) and triethylamine (1 eq vs. 1,2,3,4-tetrahydro-5-methoxy-N-propyl-naphthalen-2-amine). The biphasic system is stirred and decanted at room temperature. The lower aqueous layer is settled and separated. The organic layer is washed twice with water. The organic layer is dried by azeotropic distillation.

7.2. Preparation of (RS)-1,2,3,4-tetrahydro-5-methoxy-N-propyl-naphthalen-2-amine hydrochloride (IIa)

(R)-1,2,3,4-tetrahydro-5-methoxy-N-propyl-naphthalen-2-amine (III) (1 eq), obtained under example 7.1, is adjusted to a dilution of ~9.5 vol. in EtOAc. 1-dodecanethiol is added (1.2 eq) and the solution is heated to reflux under nitrogen atmosphere. A solution of AIBN (0.1 eq) in 0.5 vol. of EtOAc is dropwise added during 5 min. The solution is post-stirred under reflux for 30 min.

Aqueous HCl 37% w:w (1.1 eq) is added dropwise under reflux for ~5 min into the mixture obtained to precipitate the N-propyl MAT.HCl. The suspension is cooled down to 20° C. (Tramp=−20° C./h). The suspension is post-stirred at 20° C. for minimum 30 min and filtered. The cake is washed twice with EtOAc (2×1 vol.). The wet solid is dried under vacuum at 40° C. giving an off white solid. Yield: 95.0% from (III)

Example 8

Preparation of (S)-(alkoxycarbamoyl)-N-propyl-5-Methoxy-2-aminotetralin (Ib) by Chiral Chromatographic Separation of N-(alkoxycarbamoyl)-N-propyl-5-Methoxy-2-aminotetralin (IIb)

Method A: Resolution of N-(methoxycarbamoyl)-N-propyl-5-Methoxy-2-aminotetralin (Compound (IIb) Wherein $R^a$ is methyl) into (S)—N-(methoxycarbamoyl)-N-propyl-5-Methoxy-2-aminotetralin (Ib) and (R)—N-(methoxycarbamoyl)-N-propyl-5-Methoxy-2-aminotetralin (IIIb)

A feed solution of 10.5 kg of N-(methoxycarbamoyl)-N-propyl-5-Methoxy-2-aminotetralin (compound (IIb) wherein $R^a$ is methyl) in ethanol is prepared and stirred under nitrogen until complete dissolution is achieved. The solution is continuously injected in an MCC system which is equipped with six identical columns of 11.1 cm length and 4.8 cm internal diameter, in a 1-2-2-1 configuration. Each column contains 125 g of a Chiral stationary phase comprising cellulose tris (3,5-dimethylphenylcarbamate) coated onto the silica backbone and the enantiomers are separated using Ethanol as the mobile phase.

Substantially optically pure (S)—N-(methoxycarbamoyl)-N-propyl-5-Methoxy-2-aminotetralin (Ib) and (R)—N-(methoxycarbamoyl)-N-propyl-5-Methoxy-2-aminotetralin (IIb) are extracted from the stream and obtained with an enantiomeric excess greater than 99%.

Productivity of the chiral separation of compound of formula (IIb) according to Method A is 3.4 Kg of (IIb) per Kg of the Chiral Stationary Phase per day.

Method B: Resolution of N-(methoxycarbamoyl)-N-propyl-5-Methoxy-2-aminotetralin (Compound (IIb) Wherein $R^a$ is methyl) into (S)—N-(methoxycarbamoyl)-N-propyl-5-Methoxy-2-aminotetralin (Ib) and (R)—N-(methoxycarbamoyl)-N-propyl-5-Methoxy-2-aminotetralin (IIIb)

A feed solution of 10.5 kg of N-(methoxycarbamoyl)-N-propyl-5-Methoxy-2-aminotetralin (compound (IIb) wherein $R^a$ is methyl) in ethanol is prepared and stirred under nitrogen until complete dissolution is achieved. The solution is continuously injected in an MCC system which is equipped with five identical columns of 11.1 cm length and 4.8 cm internal diameter, in a 1-1, 5-1.75-075 configuration. Each column contains 125 g of a Chiral stationary phase comprising cellulose tris(3,5-dimethylphenylcarbamate) coated onto the silica backbone and the enantiomers are separated using Ethanol as the mobile phase.

Substantially optically pure (S)—N-(methoxycarbamoyl)-N-propyl-5-Methoxy-2-aminotetralin (Ib) and (R)—N-(methoxycarbamoyl)-N-propyl-5-Methoxy-2-aminotetralin (IIIb) are extracted from the stream and obtained with an enantiomeric excess greater than 99%.

Productivity of the chiral separation of compound of formula (IIb) according to Method B is 4.15 Kg of (IIb) per Kg of the Chiral Stationary Phase per day.

Method C: Resolution of N-(methoxycarbamoyl)-N-propyl-5-Methoxy-2-aminotetralin (Compound (IIb) Wherein $R^a$ is methyl) into (S)—N-(methoxycarbamoyl)-N-propyl-5-Methoxy-2-aminotetralin (Ib) and (R)—N-(methoxycarbamoyl)-N-propyl-5-Methoxy-2-aminotetralin (IIIb)

A feed solution of 3.6 g of N-(methoxycarbamoyl)-N-propyl-5-Methoxy-2-aminotetralin (compound (IIb) wherein $R^a$ is methyl) in IPA is prepared and stirred under nitrogen until complete dissolution is achieved. The solution is discontinuously injected in batch mode on a SFC system which is equipped with one column of 26 cm length and 5 cm internal diameter. This column contains 300 g of a Chiral stationary phase comprising cellulose tris(3,5-dimethylphenylcarbamate) coated onto the silica backbone and the enantiomers are separated using IPA 15% and $CO_2$ 85% as the mobile phase.

Substantially optically pure (S)—N-(methoxycarbamoyl)-N-propyl-5-Methoxy-2-aminotetralin and (R)—N-(methoxycarbamoyl)-N-propyl-5-Methoxy-2-aminotetralin are extracted from the stream and obtained with an enantiomeric excess greater than 99%.

Productivity of the chiral separation of compound of formula (IIb) according to Method C is 1.5 Kg of (IIb) per Kg of the Chiral Stationary Phase per day.

Example 9

Preparation of Compound of Formula (VIII) from Compound of Formula (Ib)

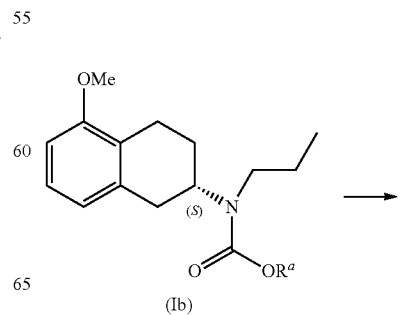

(Ib)

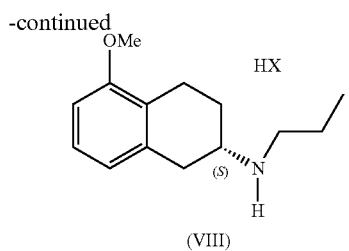

(VIII)

15 g of compound of formula (Ib) was solubilised in 30 ml (2 vol) of AcOH. 48% aqueous HBr (52.6 mL, 8.6 eq) was heated to 60-70 C and the solution of (Ib) slowly added over 25 mins. The reaction mixture is then heated (Jacket temperature 90° C.) and stirred for 30 mins. The jacket temperature is then increased to 125° C. and stirred for 6 hours. Upon reaction completion the mixture is cooled to 20° C. and 30 ml water (2 vol) added. The precipitated salt is filtered, washed with 15 mL (1 vol) and dried under vacuum at 40° C. to a constant weight. Yield=88.6%

$^1$H NMR (DMSO) δ 9.40 (1H, s, OH), 8.58 (2H, br s, NH.HBr), 6.93-6.96 (1H, m, ArH), 6.63-6.65 (1H, m, ArH), 6.55-6.57 (1H, m, ArH), 3.40 (1H, m, CH), 3.10-3.14 (1H, m, CH), 2.98 (2H, m, CH2), 2.81 (2H, m, CH2), 2.45 (1H, m, CH), 2.23 (1H, m, CH), 1.67 (3H, m), 0.93-0.96 (3H, m, CH$_3$)

Example 10

Preparation of Rotigotine from Compound of Formula (Ia)

Example 10.1

Conversion of (S)-1,2,3,4-tetrahydro-5-methoxy-N-propyl-naphthalen-2-ammonium hydrochloride (Ia) into (S)-1,2,3,4-tetrahydro-5-hydroxy-N-propyl-naphthalen-2-ammonium hydrobromide (VIII)

(S)-1,2,3,4-tetrahydro-5-methoxy-N-propyl-naphthalen-2-ammonium hydrochloride (Ia)

(60.9 g), sodium bisulfite (0.61 g), aqueous HBr (48%, 345.6 g) and glacial acetic acid (103.3 g) are combined. The batch is gradually heated to reflux and aged for a minimum of 2 hours at this temperature. On reaction completion the batch is cooled to 20±5° C. and aged at this temperature for a minimum of 1 hour. The batch is filtered and washed with water (120 mL) and dried to give 60.5 g (88.8% yield).

HPLC analyses confirmed purity >99% and 99% assay in comparison to a reference standard.

Example 10.2

Conversion of (S)-1,2,3,4-tetrahydro-5-hydroxy-N-propyl-naphthalen-2-ammonium hydrobromide (VIII) into Hydrochloride Salt of Rotigotine

10.2.1. Preparation of 2-(2-Thienyl)ethyl-4-toluene sulfonate 4-toluenesulfonyl chloride (162 g), toluene (363.3 g) and 2-(2-Thienyl)ethanol (104 g) are combined. Triethylamine (93 g) is added maintaining the temperature lower than 45° C. After 4 hrs, the mixture is washed with aqueous phosphoric acid, aqueous sodium hydroxide and then water. The organic phase is distilled off under vacuum. Isopropanol (314 g) and heptanes (365.9 g) are added. The batch is crystallized by cooling and isolated at −15° C. The crystals are filtered and washed with heptanes (175 mL). The crystals are then dried under vacuum at room temperature until a melting point of 30° C. is obtained.

Yield (214 g): 93.6%

HPLC analyses confirmed purity >99% and 100% assay in comparison to a reference standard.

10.2.2. Conversion of (S)-1,2,3,4-tetrahydro-5-hydroxy-N-propyl-naphthalen-2-ammonium hydrobromide (VIII) into Hydrochloride Salt of Rotigotine (S)-1,2,3,4-tetrahydro-5-hydroxy-N-propyl-naphthalen-2-ammonium hydrobromide (VIII) (44.5 g), sodium carbonate (24.0 g), o-xylene (390 g) and purified water (320 g) are heated to 70-80° C. and stirred until all the solids have dissolved. The pH of the aqueous phase is adjusted to 9.5-10.5 with phosphoric acid (25%). The phases are separated and the organic phase is washed with water (105 g). The organic phase is partially distilled and added to sodium carbonate (20 g). To the organic phase is added 2-(2-Thienyl)ethyl-4-toluene sulfonate (64 g) obtained in 10.2.1, sodium carbonate (0.2 g) and o-xylene (130 g) and heated to reflux. When reaction was complete by HPLC, the batch was cooled and water added (290 mL) At 75-85° C. the pH of the aqueous phase was adjusted to 9.5-10.5 with phosphoric acid (25%).

The organic layer is then washed with water (290 mL). The organic layer was extracted with a premixed solution of water (220 mL) and phosphoric acid (25%, 91 g) and then twice with water (54 mL) and phosphoric acid (25%, 18 g) at 70-90° C. The aqueous phase is passed through charcoal and celite and then toluene (270 g) and NaOH (50%, 30 g) are added. At 75-85° C., the pH of the aqueous phase was adjusted to 5.5-6.5 and the phases separated. The organic phase was washed with water and then partially distilled. At 45-55° C. 2-propanol (72 g) and rotigotine hydrochloride seeds are added. Hydrochloric acid (37%, 14 g) was slowly added. After crystallization, the batch was cooled to 15-25° C., filtered and washed with a premixed solution of toluene (60 g) and 2-propanol (20 g). The product is then dried under vacuum to a constant weight of 44.8 g.

Yield is 82%

HPLC analyses confirmed purity greater than and 100.8% assay in comparison to a reference standard.

10.3 Conversion of Rotigotine Hydrochloride to Rotigotine

Water (295 g) and rotigotine hydrochloride (120 g) followed by aqueous ammonia (25%, 111 g) and cyclohexane (295 g) are heated to reflux and agitated for 30-50 minutes. The mixture was cooled to 55-65° C. and the phases separated. Water (250 mL) is charged and the batch is heated to reflux for 30-50 minutes. The batch is cooled to 55-65° and the phases separated. The batch is then heated to reflux and cyclohexane/water is distilled until no further water is collected. The batch is then cooled to 70-78° C. If the volume of cyclohexane distilled off exceeds 15 mL then an equal amount to the cyclohexane that has been distilled off is charged to the batch. The organic phase is filtered through activated carbon and celite rinsing with cylohexane (110 g). The filterate was adjusted to 60-70° C. The batch is agitated at this temperature for 30-50 minutes. The batch is then cooled to 54-60° C. and rotigotine seed was added. After 15 minutes. The batch temperature is decreased to 37° C. in 5° C. intervals every 60 minutes. After 1 h stirring at 37° C. the batch is cooled to 25° C. and held 1 h at this temperature. The batch is then cooled and stirred at 6-12° C. for at least two hours. The slurry was then filtered and washed with cyclohexane (48 g). 101.5 g of rotigotine is obtained.

Yield is 94.4%

HPLC analyses confirmed >99% purity and 100.2% assay in comparison to a reference standard.

The invention claimed is:

1. A process of manufacture of substantially optically pure 2-aminotetralins of formula will (I) by diastereoisomeric salt resolution of compound of formula (II),

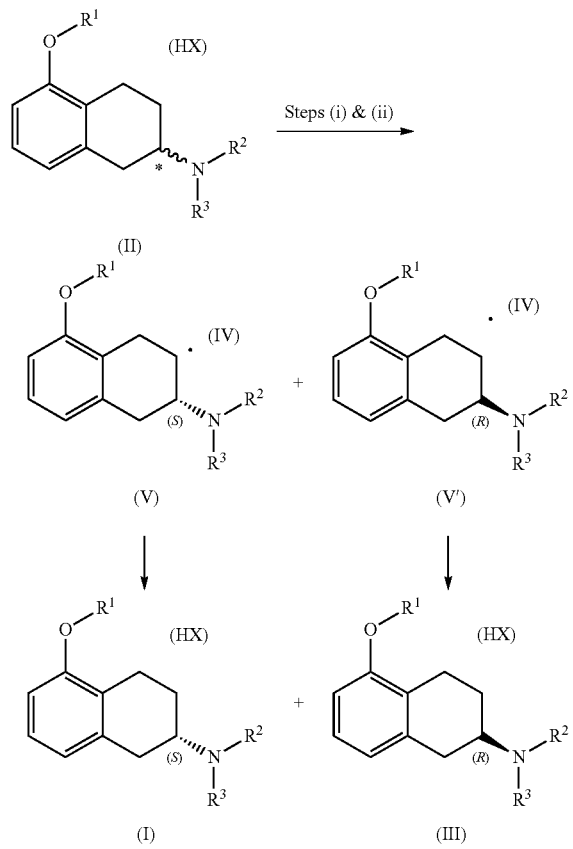

wherein salt resolution of compound of formula (II) is performed by
  (i) reacting free base of compound of formula (II) with a substantially optically pure acid (IV) selected from the group consisting of (R)-2-methoxy-2-phenyl acetic acid, (R)-2-(2-chlorophenyl)-2-hydroxyacetic acid, (S)-2-hydroxy-3-phenylpropionic acid and (R)-(–)-2-(6-methoxy-2-naphthyl)-propionic acid, in a solvent to afford diastereoisomeric salts (V) and (V'); and
  (ii) converting (V) to (I) by
    (1) crystallizing the resulting diastereoisomeric salt (V) of (i) in a solvent and
    (2) reacting said diastereoisomeric salt (V) of (ii)(1) with a mineral acid to afford the salt of compound of formula (I);
wherein $R^1$ and $R^2$ are alkyl and $R^3$ is hydrogen.

2. The process according to claim 1 wherein the free base of compound of formula (II) is obtained by treating the salt form of the compound of formula (II) with a base prior to (i).

3. The process according to claim 1 wherein diastereoisomeric salt (V') in the solvent of (ii) is recycled into the HX salt of compound of formula (II), by

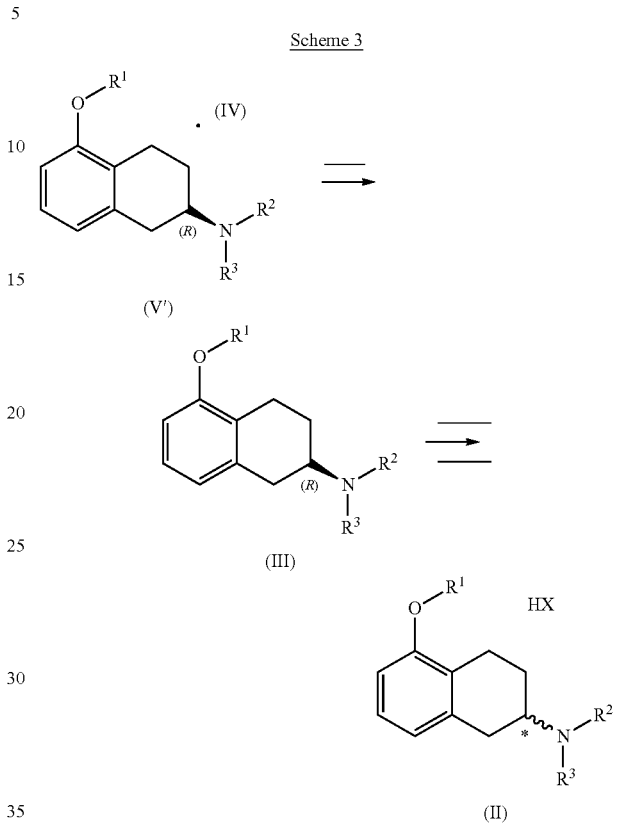

Scheme 3

(v) treating diastereoisomeric salt (V') with a base to afford the undesired enantiomer (III);
(vi) racemizing enantiomer (III) into the free base of compound of formula (II) by treatment with a racemization agent;
(vii) treating compound of formula (II) with a mineral acid HX to afford the corresponding HX salt of compound (II).

4. The process according to claim 1 wherein compound of formula (II) is 1,2,3,4-tetrahydro-5-methoxy-N-propyl-naphthalen-2-ammonium hydrochloride (IIa).

5. The process according to claim 1 wherein the salt of the compound of formula (I) is substantially optically pure (S)-1,2,3,4-tetrahydro-5-methoxy-N-propyl-naphthalen-2-ammonium hydrochloride (Ia).

6. The process according to claim 1 wherein the diastereoisomeric salt of formula (V) of (ii)(2) is selected from the group consisting of (S)-1,2,3,4-tetrahydro-5-methoxy-N-propyl-naphthalen-2-ammonium (R)-2-methoxy-2-phenylacetate (Vaa), (S)-1,2,3,4-tetrahydro-5-methoxy-N-propyl-naphthalen-2-ammonium (R)-2-(2-chlorophenyl)-2-hydroxyacetate (Vab), (S)-1,2,3,4-tetrahydro-5-methoxy-N-propyl-naphthalen-2-ammonium (S)-2-hydroxy-3-phenylpropionate (Vac), and (S)-1,2,3,4-tetrahydro-5-methoxy-N-propyl-naphthalen-2-ammonium (R) 2-(6-methoxy-2-naphthyl)-propionate (Vad).

7. The process according to claim 2 wherein the base is selected from the group consisting of sodium hydroxide, potassium hydroxide, sodium carbonate, potassium carbonate, potassium hydrogen phosphate, sodium hydrogen phosphate, potassium phosphate, sodium phosphate, diisopropylamine, triethylamine, piperidine and pyrrolidine.

8. The process according to claim 1 wherein the solvent used in (i) is selected from the group consisting of water, methanol, ethanol, propan-1-ol, propan-2-ol, methyl tert-butyl ether, tetrahydrofuran, 2-methyl tetrahydrofuran, methyl acetate, ethyl acetate, isopropyl acetate and a mixture of two or more of these solvents.

9. The process according to claim 8 wherein a mixture of water and one or more solvents selected from the group consisting of methanol, ethanol, propan-1-ol, propan-2-ol, methyl tert-butyl ether, tetrahydrofuran, 2-methyl tetrahydrofuran, methyl acetate, ethyl acetate, and isopropyl acetate is used.

10. The process according to claim 9 wherein the aqueous phase is discarded prior to crystallization of diastereoisomeric salt (V) and the remaining organic phase is cooled at a temperature comprised between −10° C. and 0° C.

11. The process according to claim 3 wherein racemization in (vi) is radical mediated racemization.

12. The process according to claim 1 wherein the mineral acid is selected from the group consisting of hydrochloric acid, hydrobromic acid, hydroiodic acid, sulfuric acid and phosphoric acid.

13. The process according to claim 1 which has a resolvability of between about 0.45 and about 0.90 and wherein the resolvability is represented by S and is defined as the product of the yield of the diastereoisomeric salt and the diastereoisomeric excess of the isolated diastereoisomeric salt.

14. A salt (V) selected from the group consisting of (S)-1,2,3,4-tetrahydro-5-methoxy-N-propyl-naphthalen-2-ammonium (R)-2-methoxy-2-phenylacetate, (S)-1,2,3,4-tetrahydro-5-methoxy-N-propyl-naphthalen-2-ammonium (R)-2-(2-chlorophenyl)-2-hydroxyacetate, (S)-1,2,3,4-tetrahydro-5-methoxy-N-propyl-naphthalen-2-ammonium (S)-2-hydroxy-3-phenylpropionate, and (S)-1,2,3,4-tetrahydro-5-methoxy-N-propyl-naphthalen-2-ammonium (R) 2-(6-methoxy-2-naphthyl)-propionate.

15. A process of manufacture of rotigotine, and salts thereof, using a salt (V) according to claim 14 as synthetic intermediate.

16. The process according to claim 5, further comprising manufacture of rotigotine (IX), or salts thereof, starting from compound of formula (Ia):

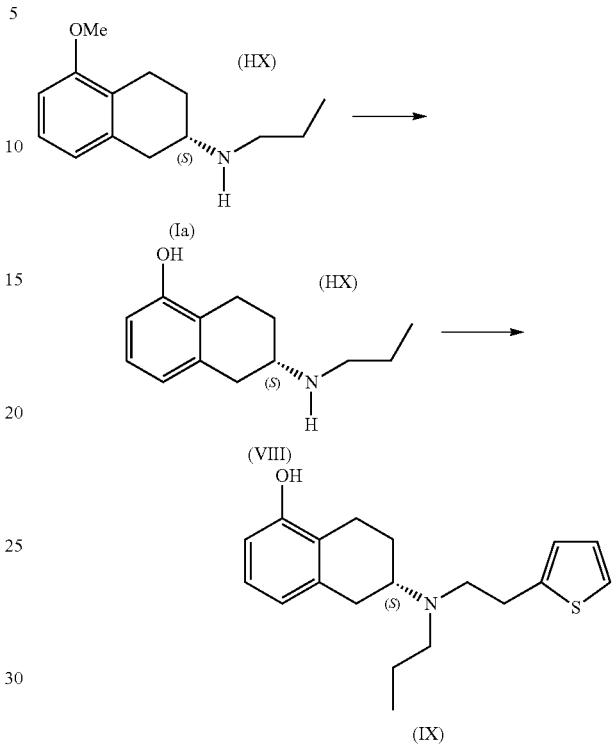

(a) reacting compound of formula (Ia) with aqueous HBr in the presence of acetic acid;
(b) reacting compound of formula (VIII) obtained as a result of (a) with 2-(2-thienyl)ethanolbenzenesulfonate or 2-(2-thienyl) ethanol toluenesulfonate in the presence of an alkali metal carbonate or an alkali metal bicarbonate.

* * * * *